US010047163B2

(12) United States Patent
Liu

(10) Patent No.: US 10,047,163 B2
(45) Date of Patent: Aug. 14, 2018

(54) MULTISPECIFIC CONSTRUCTS

(71) Applicant: AbbVie Stemcentrx LLC, North Chicago, IL (US)

(72) Inventor: David Liu, San Francisco, CA (US)

(73) Assignee: AbbVie Stemcentrx LLC, North Chicago, IL (US)

( * ) Notice: Subject to any disclaimer, the term of this patent is extended or adjusted under 35 U.S.C. 154(b) by 82 days.

(21) Appl. No.: 14/765,861

(22) PCT Filed: Feb. 7, 2014

(86) PCT No.: PCT/US2014/015409
§ 371 (c)(1),
(2) Date: Aug. 5, 2015

(87) PCT Pub. No.: WO2014/124326
PCT Pub. Date: Aug. 14, 2014

(65) Prior Publication Data
US 2015/0368352 A1    Dec. 24, 2015

Related U.S. Application Data

(60) Provisional application No. 61/762,755, filed on Feb. 8, 2013.

(51) Int. Cl.
| C07K 16/28 | (2006.01) |
| C07K 16/46 | (2006.01) |
| C07K 16/18 | (2006.01) |
| C07K 16/22 | (2006.01) |

(52) U.S. Cl.
CPC ...... *C07K 16/2896* (2013.01); *C07K 16/2803* (2013.01); *C07K 16/468* (2013.01); *C07K 2317/31* (2013.01); *C07K 2317/52* (2013.01); *C07K 2317/522* (2013.01); *C07K 2317/55* (2013.01); *C07K 2317/77* (2013.01); *C07K 2317/92* (2013.01)

(58) Field of Classification Search
CPC .... C07K 16/18; C07K 16/2803; C07K 16/00; C07K 16/2896; C07K 16/468; C07K 2317/92; C07K 2317/52; C07K 2317/522; C07K 2317/77; C07K 2317/55; C07K 2317/31
See application file for complete search history.

(56) References Cited

U.S. PATENT DOCUMENTS

| 7,183,076 B2 | 2/2007 | Arathoon et al. |
| 7,521,056 B2 | 4/2009 | Chang et al. |
| 8,216,805 B2 | 7/2012 | Carter et al. |
| 8,349,332 B2 | 1/2013 | Chang et al. |
| 2009/0130105 A1 | 5/2009 | Glaser et al. |
| 2009/0155255 A1 | 6/2009 | Glaser et al. |
| 2010/0015133 A1 | 1/2010 | Igawa et al. |
| 2010/0286374 A1 | 11/2010 | Kannan et al. |
| 2011/0123532 A1 | 5/2011 | Gurney et al. |
| 2011/0301331 A1 | 12/2011 | Glaser et al. |
| 2012/0078028 A1 | 3/2012 | Satpayev et al. |
| 2012/0121596 A1 | 5/2012 | Fuh et al. |
| 2012/0149876 A1 | 6/2012 | Von Kreudenstein et al. |
| 2012/0316324 A1 | 12/2012 | Adams et al. |
| 2013/0004416 A1 | 1/2013 | Wu et al. |
| 2013/0017200 A1 | 1/2013 | Scheer et al. |
| 2013/0058947 A1 | 3/2013 | Stull et al. |
| 2013/0061340 A1 | 3/2013 | Dylla et al. |
| 2013/0061342 A1 | 3/2013 | Dylla et al. |
| 2013/0089554 A1* | 4/2013 | Blankenship ...... C07K 16/2818 424/136.1 |
| 2013/0260385 A1 | 10/2013 | Dylla et al. |
| 2014/0154254 A1* | 6/2014 | Kannan .................. C07K 16/18 424/136.1 |
| 2014/0370020 A1* | 12/2014 | Kuramochi ........ C07K 16/2866 424/136.1 |
| 2015/0030636 A1 | 1/2015 | Dylla et al. |

FOREIGN PATENT DOCUMENTS

| WO | WO 1994/004690 A1 | 3/1994 |
| WO | WO 1996/027011 A1 | 9/1996 |
| WO | WO 2001/077342 A1 | 10/2001 |
| WO | WO 2006/106905 A1 | 12/2006 |
| WO | WO 2012/031280 A2 | 3/2012 |
| WO | WO 2012/118547 A1 | 9/2012 |
| WO | WO 2012/162583 A1 | 11/2012 |
| WO | WO 2013/005194 A2 | 1/2013 |
| WO | WO 2013/119964 A2 | 8/2013 |
| WO | WO 2015/031698 A1 | 3/2015 |

(Continued)

OTHER PUBLICATIONS

Jiang et al., J. Biol. Chem. 280 (6): 4656-4662, Feb. 11, 2005.*
Stancovski et al., Proceedings of the National Academy of Science USA 88: 8691-8695, 1991.*
Riemer et al., Mol. Immunol. 42: 1121-1124, 2005.*
Yu et al., Investigative Ophthalmology & Visual Science 49(2): 522-527, Feb. 2008.*
Witte et al., Cancer and Metastasis Reviews 17: 155-161, 1998.*
Wu et al., J Mol Biol 294: 151-162, 1999.*
Colman et al., in Research in Immunology (145(1):33-36, 1994.*
Dufner et al., Trends Biotechnol 24(11): 523-529, 2006.*
Cochran et al., J. Immunol. Meth. 287: 147-158, 2004.*

(Continued)

*Primary Examiner* — Phuong Huynh

(74) *Attorney, Agent, or Firm* — Womble Bond Dickinson (US) LLP

(57) ABSTRACT

Provided are novel multispecific antibody constructs and multispecific antibody drug conjugates (ADCs), and methods of using such antibodies and ADCs to treat cancer. IgG-like bispecific antibodies have different binding specificities on each arm of the antibody. They are similar in structure to monospecific IgGs in that they contain two heavy chains with VH, CH1, CH2 and CH3 regions, and two light chains with VL and CL regions.

3 Claims, 9 Drawing Sheets

(56) References Cited

FOREIGN PATENT DOCUMENTS

WO  WO 2016/064749  4/2016

OTHER PUBLICATIONS

Rudikoff et al., Proceedings of the National Academy of Sciences, 79:1979-1983, 1982.*
Brennan et al., "Preparation of Bispecific Antibodies by Chemical Recombination of Monoclonal Immunoglobulin G1 Fragments," *Science*, Jul. 5, 1985, 229: 81-83.
Coloma, M.J., et al., "Design and production of novel tetravalent bispecific antibodies," *Nature Biotech*, Feb. 1997, 15(2): 159-163.
Davis JH et al., "SEEDbodies: fusion proteins based on strand-exchange engineered domain (SEED) $C_H3$ heterodimers in an Fc analogue platform for asymmetric binders or immunofusions and bispecific antibodies," *Protein Eng Des Sel*, Apr. 2010, 23(4): 195-202.
Gunasekaran et al., "Enhancing Antibody Fc Heterodimer Formation through Electrostatic Steering Effects," Jun. 18, 2010, *J. Biol Chem.*, 285(25): 19637-19646.
Kontermann, "Dual targeting strategies with bispecific antibodies," *Landes Bioscience, mAbs*, 2012, 4(2): 182-197.
Merchant et al., "An efficient route to human bispecific IgG," *Nat. Biotechnol.*, Jul. 1998, 16(7): 677-681.
Milstein et al., "Hybrid hybridomas and their use in immunohistochemistry," *Nature*, 1983, 305(5934): 537-40.
Moore et al., "A novel bispecific antibody format enables simultaneous bivalent and monovalent co-engagement of distinct target antigens," Mabs, 2011, 3:546-567.
Morrison, S.L., "Two heads are better than one," *Nature Biotech.*, 2007, 25: 1233-1234.
Protein Data Bank (PDB) model ID 2XRA, "crystal structure of the HK20 Fab in complex with a gp41 mimetic 5-Helix," 2010.
Protein Data Bank (PDB) model 3DVN, "Crystal structure of K63-specific fab Apu2.16 bound to K63-linked di-ubiquitin," 2008.
Raso et al., "Intracellular Targeting with Low pH-triggered Bispecific Antibodies," *J. Biol. Chem.*, 1997, 272: 27623.
Ridgway et al., "'Knobs-into-holes' engineering of antibody CH3 domains for heavy chain heterodimerization," 1996, *Protein Eng.* 9(7): 617-621.
Suresh et al., "Bispecific Monoclonal Antibodies from Hybrid Hybridomas," 1986, *Methods in Enzymology*, 121: 210-28.
Extended European Search Report dated Aug. 22, 2016, issued in European patent application (No. 14749020.5).
Search Report dated Apr. 28, 2014, issued in International application (No. PCT/US2014/015409).
Written Opinion dated Apr. 28, 2014, issued in International application (No. PCT/US2014/015409).
International Preliminary Report on Patentability dated Aug. 11, 2015, issued in International application (No. PCT/US2014/015409).

* cited by examiner

MULTISPECIFIC CONSTRUCTS

CROSS REFERENCED APPLICATIONS

This is a national stage application of PCT/US2014/015409 filed on Feb. 7, 2014, which claims priority from U.S. Provisional Application No. 61/762,755 filed on Feb. 8, 2013, which is incorporated herein by reference in its entirety.

FIELD OF THE INVENTION

This application generally relates to improved methods of generating multispecific antibodies capable of binding two or more antigens, the resulting compounds and compositions and their use in clinical and non-clinical applications.

BACKGROUND OF THE INVENTION

IgG-like bispecific antibodies have different binding specificities on each arm of the antibody. They are similar in structure to monospecific IgGs in that they contain two heavy chains with VH, CH1, CH2 and CH3 regions, and two light chains with VL and CL regions. However, in order to create different specificities on each arm, IgG-like bispecific antibodies preferably have two different heavy chains (at least in the VH regions) that pair in heteromeric or asymmetric fashion as opposed to homodimerically. In addition, assembly of functional bispecific molecules requires complementary pairing of two distinct light chains (different at least in the VL region) to their respective heavy chains.

Various strategies have been proposed to solve the problem of asymmetric heavy chain pairing. One method is to mutate the CH3 domains of the antibodies in order to favor their heterodimerization (i.e. pairing of heavy chain A with heavy chain B) and to prevent their homodimerization. A well known embodiment of this methodology involves the "knob into holes" approach (Ridgeway et al., 1996, Protein Eng. 9(7): 617-621). A "knob" mutation, consisting of the replacement of a small amino-acid by a larger one, is introduced at the CH3 dimer interface of the heavy chain of antibody A, resulting in a steric hindrance which prevents homodimerization. Concurrently in order to promote heterodimerization, a complementary "hole" mutation, consisting of the replacement of a large amino acid by a smaller one, is introduced into the CH3 domain of antibody B.

Another method is the use of electrostatics, wherein the CH3 domain interface of the antibody Fc region is modified with selected mutations to create altered charge polarity across the Fc dimer interface such that coexpression of electrostatically matched Fc chains support favorable attractive interactions thereby promoting desired Fc heterodimer formation, whereas unfavorable repulsive charge interactions suppress unwanted Fc homodimer formation (see e.g., Gunasekaran et al., 2010, *J Biol Chem.* 285(25): 19637-19646, WO/2006/106905, U.S. Patent Application 2011/0123532 each of which is incorporated herein by reference). Yet other methods for asymmetric heavy chain pairing have also been published (see Merchant et al., 1998, Nat Biotechnol 16: 677-681; Moore et al., 2011, MAbs 3:546-567; and Davis J H et al., 2010, Protein Eng Des Sel 23: 195-202 and U.S. Patent Application 2012/0149876 each which are accomplished herein by reference).

Quadroma technology has also been used to create bispecific antibodies. Quadroma technology (Milstein and Cuello, 1983, Nature, 305(5934): p. 537-40) is based on the somatic fusion of two different hybridoma cell lines expressing murine monoclonal antibodies with the desired specificities of the bispecific antibody. But because of the random pairing of two different Ig heavy and light chains within the resulting hybrid-hybridoma (or quadroma) cell line, up to ten different immunoglobulin species are generated of which only one is the functional bispecific antibody. The presence of heavy chain/light chain mispaired by-products and significantly reduced production yields means that sophisticated purification procedures are required to obtain functional bispecific antibodies in sufficient quantities.

In an attempt to reduce heavy chain/light chain mispairing, methods were employed using antibodies having different specificities but sharing a common light chain, previously identified from an scFv phage library (see e.g., Merchant et al., 1998, Nat Biotechnol 16: 677-681; U.S. Pat. No. 7,183,076). The drawback of this approach is the difficulty in identifying antibodies having a common light chain. That is, while it is possible for antibodies to be engineered to bind antigen with negligible energetic contribution of the light chain thus allowing for a common light chain to be used when engineering a bispecific IgG, it is more common for antibodies to require energetic contributions of both the heavy chain and light chain for high affinity binding to antigen. When two monospecific antibodies are reformatted as a single bispecific antibody, the correct pairing of each heavy chain with their corresponding light chain becomes important for the retention of binding properties of the original monospecific IgG antibodies. This significantly limits the usage of common light chains when reformatting existing antibodies as bispecifics. Without additional molecular mechanisms to ensure correct heavy/light chain pairing, coexpression of the two heavy chains and two light chains would result in mixed products with mispaired heavy and light chains.

Despite such attempts there is a need in the art for improved methods of producing multispecific antibodies, including bispecific antibodies, that exhibit relatively high fidelity in pairing heavy and light chains and provide assembled constructs that have high affinity for both antigens.

SUMMARY OF THE INVENTION

To this end the present invention provides novel methods, compounds and compositions that provide for improved pairing of antibody heavy and light chains in multispecific constructs. As used herein and described in more detail below the term "multispecific constructs" shall mean any antibody or antibody component that possesses the ability to simultaneously bind to at least two antigenic determinants. More particularly, in preferred embodiments the instant invention provides for the selective substitution of certain amino acid residues in the CH1 (antibody heavy chain constant region 1) and CL (light chain constant region) domains with charged amino acid residues in order to take advantage of electrostatic forces such that the correct pairing of corresponding heavy and light chains is favored and incorrect pairing of non-corresponding heavy and light chains is disfavored. It will be appreciated that such modified CH1 and CL domains preferentially provide for the assembly of multispecific constructs. In certain preferred embodiments the disclosed pairing mechanisms favoring preferential assembly of selected heavy and light chains may be used to provide bivalent, trivalent or tetravalent constructs comprising, for example, IgG-Fab fusions.

More specifically preferred embodiments of the instant invention provide multispecific constructs where selected amino acids in the CH1 and/or CL (i.e., kappa or lambda light chain constant regions) are mutated to alter the charge distribution of the chains and improve assembly and stability of the multispecific antibodies. Mutations to the respective constant regions of each chain are introduced for the purpose of either: (i) preferentially pairing heavy chains of different specificity in heteromeric rather than homomeric fashion (asymmetric heavy chain pairing) or (ii) preferentially pairing each heavy chain with a preselected corresponding light chain (heavy chain/light chain pairing) to provide constructs having immunospecificity for at least two determinants. As seen in the Examples below these constructs are particularly effective in mediating cell killing.

DETAILED DESCRIPTION OF THE INVENTION

I. Introduction

Figure 1:
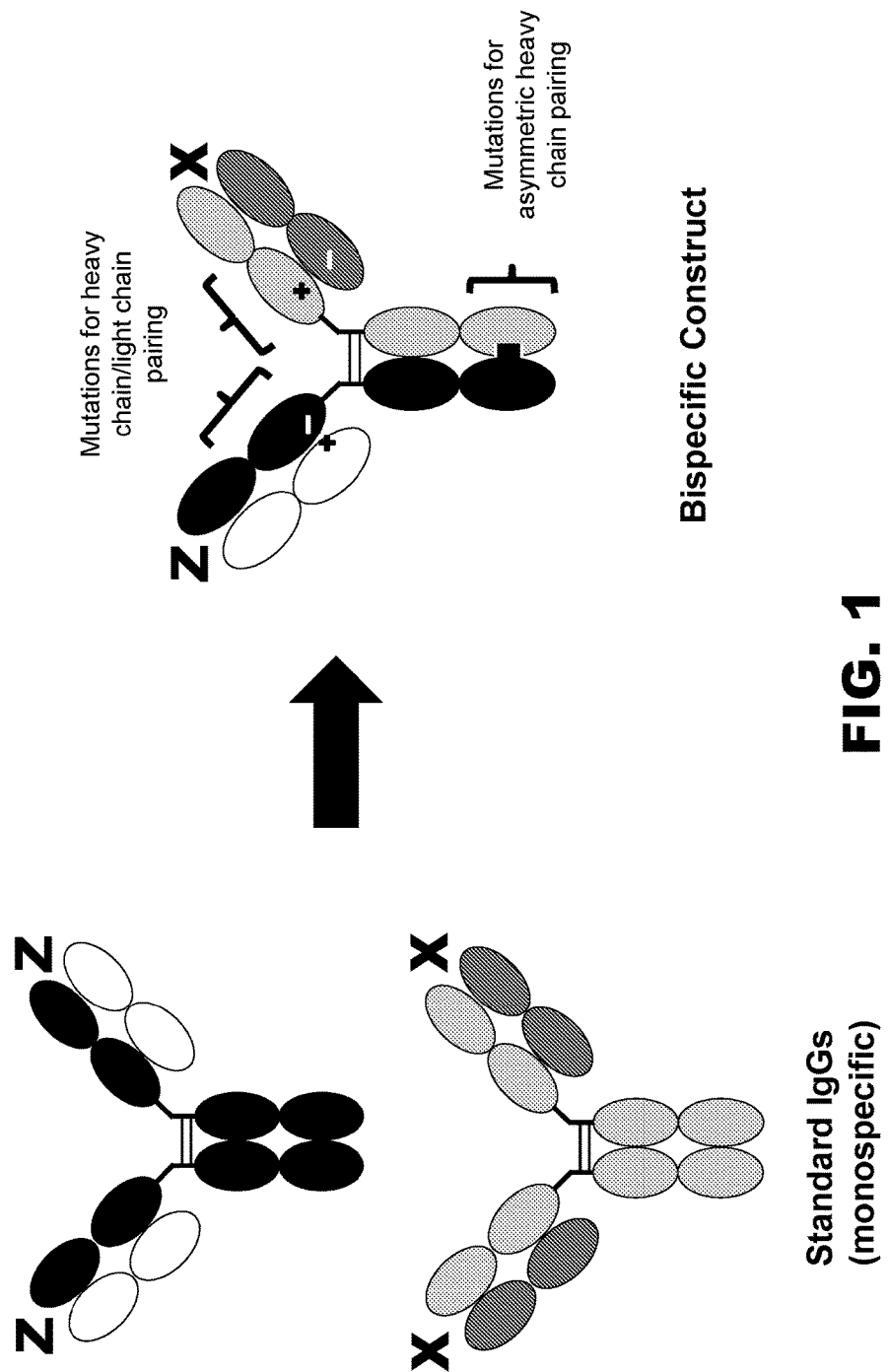
FIG. 1 shows a schematic diagram of standard bivalent monospecific antibodies, and a bispecific antibody construct of the instant invention where X and Z represent distinct immunogenic determinants. The exemplary bispecific antibody comprises two heavy chains that pair in heterodimeric fashion, and corresponding light chains that preferentially pair with the correct heavy chains due to charged residue substitutions at the CH1 and CL domains.

The present invention may be embodied in many different forms. Disclosed herein are specific, non-limiting, illustrative embodiments thereof that exemplify the principles of the invention. Any section headings used herein are for organizational purposes only and are not to be construed as limiting the subject matter described. For the purposes of the instant disclosure all identifying sequence accession numbers may be found in the NCBI Reference Sequence (RefSeq) database and/or the NCBI GenBank® archival sequence database unless otherwise noted.

This invention generally pertains to a novel method of generating multispecific antibodies, including bispecific antibodies, capable of binding at least two antigenic determinants with high affinity. In this regard it is important to note that the discrete determinants may be present on the same antigen (e.g., a protein) or cell or may be present on different antigens or cells. More particularly, it has surprisingly been found that multispecific antibodies may be preferentially assembled through the imposition and appropriate dispersion of electrostatic charges along selected components or domains of the antibody components. That is, by imparting certain electrostatic charges to specific antibody domains, particularly CH1 and CL domains, the inventors have discovered that defined multispecific antibody constructs may preferentially be assembled. In particularly preferred embodiments the imposition of the electrostatic charges is effected through the elimination, substitution or mutation of selected amino acid residues (e.g., uncharged for charged) at the appropriate position of the source antibody component. Without imposition of the selected electrostatic charges the secreted and soluble source antibody components assemble in a non-directed fashion to produce a substantially homogenous mixture of desired and undesired antibodies comprising inoperative (i.e., nonbinding), monospecific and multispecific constructs. Such non-driven assembly provides substantially lower yields of the desired multispecific construct thereby raising costs and complicating purification protocols. Conversely, using the disclosed methods the yield of the desired multispecific construct is dramatically increased and production of misassembled, inoperative and hard to separate constructs is significantly reduced.

II. Multispecific Antibodies

As will be discussed in detail below and in the appended Examples, monospecific antibodies used to fabricate the multispecific constructs of the instant invention may be obtained from a variety of sources. By way of example such "source" antibodies may be generated using conventional immunization and hybridoma techniques or obtained from animals engineered to provide fully human antibodies. In other embodiments source antibodies may be obtained, derived or generated from known or commercially available antibodies, including those therapeutic and diagnostic antibodies that are presently being used in the clinic or are in clinical trials. Essentially, any monospecific antibody for which the nucleic acid or amino acid sequence of the heavy and/or light chain variable region is derived or known may serve as a source antibody for the purposes of the instant disclosure and may be used to fabricate the multispecific antibodies of the instant invention.

While the disclosed multispecific constructs may incorporate a wide variety of source antibodies (or fragments thereof) it will be appreciated that the present invention is largely predicated on the preferential assembly of the desired product. As indicated, the preferential assembly of the construct may be driven by the selected imposition of electrostatic charges to the binding region of one or more source antibodies or fragments thereof through the deletion, substitution, mutation or elimination of certain amino acid residues. In particularly preferred embodiments the position of the altered amino acid residues will be located in the CH1 or CL domains of one or more source antibodies or fragments thereof. In other preferred embodiments opposite electrical charges (i.e., + and −) will be generated and/or imposed in respective heavy and light chain binding regions where assembly is desirable. Driven by the attraction of the opposite charges the altered heavy and light chains preferentially associate in a non-covalent fashion. By distributing the appropriate charges to drive association of specific heavy and light chain binding regions, preselected multispecific constructs may be preferentially assembled.

For example, as shown in FIG. 1 a multispecific antibody of the instant invention is generated by specifically imposing and distributing positive and negative charges on selected heavy and light chain binding regions. More particularly, the amino acid sequences in the two monospecific source antibodies were altered to impart a positive or negative charge in the respective CH1 or CL domain of the selected antibody. In this regard the CH1 domain of monospecific antibody 1 (black oval) is altered to impart a negative charge while the CL domain of the same antibody (white oval) is altered to impart a positive charge. Conversely, in monospecific antibody 2 the CH1 domain (light gray oval) is altered to exhibit a positive charge while the CL domain (dark gray oval) is altered to exhibit a negative charge. Additionally, the Fc regions of both heavy chains are engineered to exhibit a "knobs into holes" configuration (see e.g., U.S. Pat. No. 8,216,805) to promote heavy chain heterodimerization. Upon secretion the two heavy chains are driven to assemble asymmetrically by the knobs into holes configuration of their respective Fc regions. Significantly, due to the imposed charges the two altered light chains preferentially associate with the appropriate (in the sense of having the opposite imparted charge) heavy chain to provide two binding sites with different antigen specificities (X and Z). In accordance with the teachings herein, assembly of light chain/heavy chain pairs having the same charge in the CH1/CL domains is strongly disfavored and occurs only rarely.

Those of skill in the art will appreciate that various methods exist to promote asymmetric association of the selected heavy chains. For example, preferential heterodimerization of heavy chains may be achieved by imparting opposite charges in complementary positions of the Fc region. In selected embodiments the imposition of electrostatic charges will promote the formation of heterodimeric pairs while discouraging the formation of homodimeric pairs. Moreover, due to the surface configuration of the Fc region and associated distribution of forces, the imposition of such charges should not significantly interfere with the preferential assembly of the heavy and light chain binding regions. In addition, art-recognized techniques besides "knobs into holes" (e.g., chemical linkage, molecular engineering to form covalent bonds, disulfide linkage, etc.) may be used to promote heavy chain heterodimerization as discussed herein below.

Figure 2:
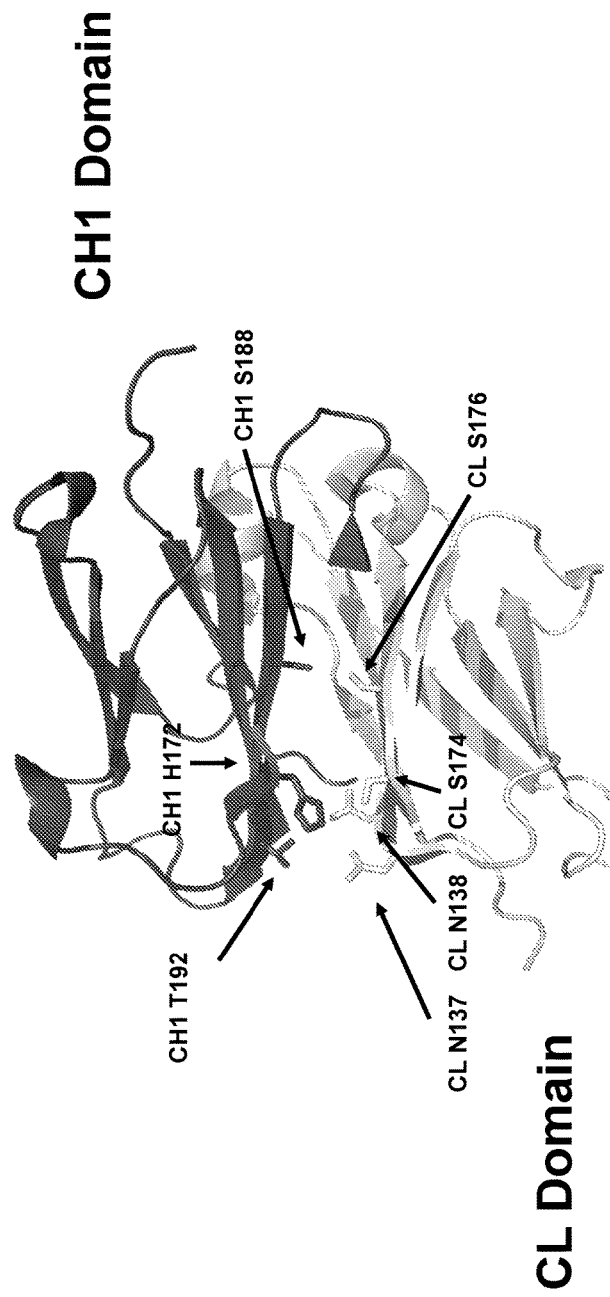
FIG. 2 shows a ribbon-structure diagram with candidate residues for substitutions highlighted. CH1 is shown in dark gray and CL is shown in light gray. Residues 164-172 from the CL domain and 174-176 and 130-137 from CH1 domains have been omitted for clarity. Numbering is based on the Kabat numbering scheme.

Preferred embodiments of the instant invention impart or generate the desired site specific electrostatic charge by deletion, substitution or mutation of certain amino acid residues at the appropriate position. Upon presentation of appropriate heavy and/or light chain sequences one of skill in the art could, in view of the instant teachings, discern appropriate positions or residues that may be altered to provide the desired charge distribution. In this regard and as shown in more detail in the appended Examples, residue positions amenable to alteration and charge imposition in accordance with the instant invention may be determined using art-recognized crystallography techniques and computer modeling. More specifically, in certain embodiments crystal structures of the selected antibody binding regions may be analyzed using the Protein Data Bank (PDB; maintained by Research Collaboratory for Structural Bioinformatics) to provide heavy and light chain residue positions that are relatively proximal to each other. FIG. 2 shows the results of an exemplary analysis undertaken in accordance with the teachings herein. In this example the analysis provided the three dimensional structure of a CH1 domain and a CL kappa domain along with seven residues (three on CH1 and four on CL) that are relatively proximal to each other and provide good candidates for replacement. Besides the identification of such residues additional information regarding adjacent residues, potential steric hindrance and heavy and light chain interface configurations may also be obtained. Taken together such information may be used to determine which residues may then be altered to impart an effective positive or negative charge at the selected position of the heavy or light chain.

More specifically, certain preferred embodiments of the instant invention will comprise altering the electrostatic charge distribution in the CL domain or the CH1 domain of an IgG1 source antibody. In selected embodiments and as shown in the appended Examples, the CL domain will comprise a kappa CL domain. In other embodiments the source antibody may comprise a lambda CL domain. As the sequences of all human IgG CL domains are well known, one skilled in the art may easily analyze both lambda and kappa sequences in accordance with the instant disclosure and employ the same to provide compatible multispecific antibody constructs. Similarly, for the purposes of explanation and demonstration the following discussion and appended Examples will primarily feature the IgG1 CH1 domain. As with the light chain constant region all human CH1 domain sequences from different isotypes (IgM, IgD, IgE, IgA) and subclasses (IgG1, IgG2, IgG3, IgG4, IgA1, IgA2) are well known and characterized. Accordingly, one skilled in the art may readily exploit source antibodies comprising any isotype or subclass and alter or modify the electrostatic charge distribution in each discrete domain as taught by the instant disclosure to provide the multispecific antibodies of the present invention.

When the desired construct employs a kappa CL domain preferred embodiments will comprise amino acid substitutions N137X, N138X, S176X and S174X wherein X may be selected from any charged amino acid including arginine, lysine, histidine, aspartic acid and glutamic acid. Similarly, when the desired construct employs an IgG1 CH1 domain preferred embodiments will comprise amino acid substitutions H172X, S188X and T192X wherein X may be selected from any charged amino acid including arginine, lysine, histidine, aspartic acid and glutamic acid. It will be appreciated that, in accordance with the instant teachings the precise substitutions will be made to optimize the distribution of opposite electrostatic charges and promote the efficient assembly of the desired heavy and light chains.

More generally, as discussed herein the identified residues or heavy or light chain position may be altered in a number of ways using molecular biology or biochemical techniques that are standard in the art. In this respect the selected amino acid residues may be deleted, substituted with other residues, or randomly mutated and screened to determine the subsequent impact on charge distribution. When an identified residue is to be replaced or substituted the replacement amino acid preferably comprises a positively or negatively charged natural or non-natural amino acid (i.e., those not naturally found in humans). In particularly preferred embodiments the amino acid will comprise a natural charged amino acid selected from the group consisting of arginine, lysine, histidine, aspartic acid and glutamic acid. Those skilled in the art will appreciate that if the charge to be imparted is positive the selected replacement amino acid shall comprise lysine, arginine or histidine whereas if the desired charge is negative the replacement amino acid shall comprise aspartic acid or glutamic acid. In selected embodiments the amino acids placed in one chain will comprise lysine, arginine or histidine while the amino acids incorporated in the corresponding opposite chain will comprise aspartic acid or glutamic acid. The precise selection of which replacement amino acid to insert will depend on the desired strength of the charge, the fit of the amino acid in the position and the surrounding electrostatic environment (including any charges placed on the complementary chain), each of which may readily be determined without undue experimentation. Moreover, any replacement amino acids may be placed or inserted in non-contiguous positions to optimize the charge distribution while maintaining the wild type residue composition and configuration of the heavy and light chain interface to the extent possible.

Figure 6:
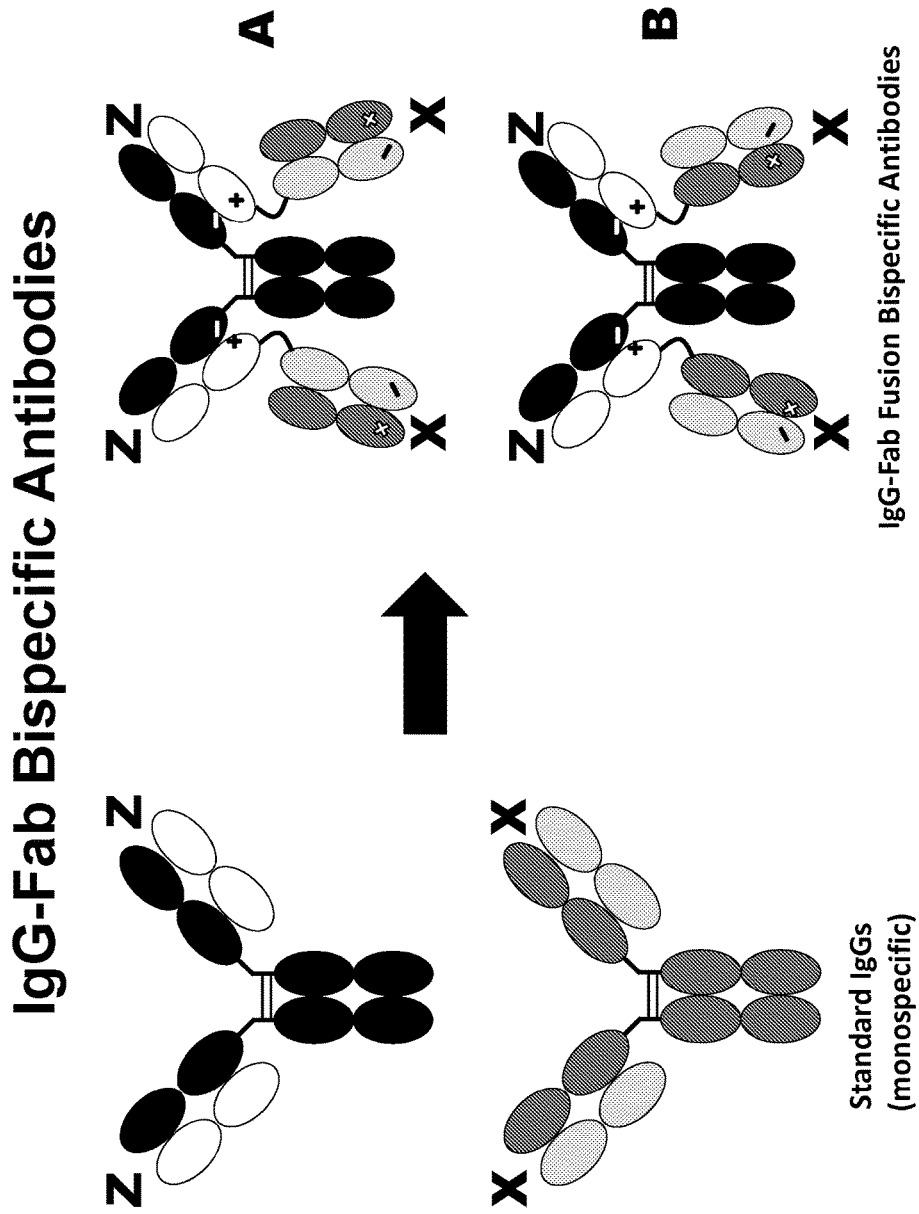
FIG. 6 shows a schematic diagram of two standard bivalent monospecific antibodies, and two exemplary tetravalent bispecific antibody constructs (i.e., IgG-Fab constructs) of the instant invention where X and Z represent distinct immunogenic determinants. The exemplary constructs comprise homodimeric full length heavy chains (black ovals) that, in accordance with the teachings herein are preferentially paired with a light chain (white ovals) due to imposed electrostatic charges wherein the light chain is covalently linked to a second light chain (construct A, light gray ovals) or a CH1/VH (construct B, dark gray ovals) antibody fragment.

In addition to the exemplary construct shown in FIG. 1 it will be appreciated that the methods and principles of the instant invention may be used to provide various multispecific constructs in accordance with the instant disclosure. That is, the use of imposed charge distribution for the preferential assembly of multispecific constructs provides for multiple configurations of compatible antibodies. In this regard FIG. 6 depicts a putative exemplary tetravalent bispecific antibody comprising IgG-Fab constructs. Through the placement of positive and negative charges in selected domains preferential assembly of the construct may be achieved. More specifically, negative charges are imparted to the CH1 domain of monospecific source antibody 1 (black oval) while positive charges are imparted to the CL domain of the same antibody (white oval). Conversely, in monospecific source antibody 2 positive charges are imparted to the CH1 domain of the heavy chain (dark gray oval) while negative charges are imparted to the CL domain of the light chain (light gray oval). Standard molecular biology techniques are then used to engineer single chain constructs comprising the light chain binding region of antibody 1 covalently linked to either; i) the light chain binding region of antibody 2 (construct A) or ii) the heavy chain binding region of antibody 2 (construct B). Upon secretion of the three construct chains (antibody 1 heavy chain, antibody 2 light or heavy chain binding region and light chain—Fab) the bispecific tetravalent constructs A and B are preferentially assembled and react with determinants X and Z. Unlike the exemplary embodiment depicted in FIG. 1, the multispecific constructs of FIG. 6 comprises a homodimeric heavy chain. Further, the natural conformation and resulting interfaces of the heavy and light chains substantially inhibit the pairing of the two light chains or the two heavy chain binding regions despite the imposition of opposite charges.

As alluded to above, the imposition of electrostatic charges in accordance with the instant invention drives formation of the desired constructs while inhibiting the formation of unwanted (e.g., monospecific) constructs and inoperative (e.g., partially or wholly non-binding) constructs. That is, the methods of the present invention provide for the preferential assembly of the desired multispecific antibodies. As used herein the term "preferential assembly" shall mean that the desired multispecific construct is produced or assembled at a rate higher than would be obtained if electrostatic charges were not imparted as set forth herein. This preferential assembly rate may be measured and quantified as the percentage of appropriately assembled operative multispecific construct present in the supernatant of engineered cells expressing the charged antibody components. In this regard the present invention provides that operable multispecific constructs will be present in cell supernatants at greater than about 20%, about 25%, about 30%, about 35%, about 40%, about 45%, about 50%, or even about 55% purity as a percentage of all constructs (e.g., including incorrectly assembled/inoperative constructs). As shown in the Examples below the characterization of "operable multispecific constructs" may be accomplished through a combination of binding assays (ForteBio, Biacore, ELISA, etc.) and molecular configuration analysis (mass spectrometry, chromatography, gel electrophoresis, etc.). Such analytical techniques are well known in the art and may readily be employed by a skilled artisan to determine the degree of operable multispecific purity. In preferred embodiments the cell supernatant will comprise operable multispecific constructs at a purity of greater than about 60%, about 62%, about 64%, about 66%, about 68%, about 70%, about 72%, about 74%, about 76%, about 78% or even about 80%. In particularly preferred embodiments the cell supernatant will comprise operable multispecific constructs at a purity of greater than about 82%, about 84%, about 86%, about 88%, about 90%, about 92% or even about 95%.

It will further be appreciated that the effectiveness of the instant invention (or preferential assembly) may also be quantified empirically by comparing the final concentration of the disclosed constructs with equivalent constructs lacking the imposed electrostatic charges. That is, one skilled in the art could prepare discrete cell lines expressing multispecific constructs with and without the imposed electrostatic charges and compare the yield of operable multispecific constructs from each cell line. As discussed above the characterization of operable multispecific constructs may be accomplished through a combination of binding assays (ForteBio, Biacore, ELISA, etc.) and molecular configuration analysis (mass spectrometry, chromatography, gel electrophoresis, etc.). Assuming the expression levels of the discrete cell lines are equivalent or accounted for, the supernatant concentration of charged operable multispecific constructs of the present invention will be at least 5% greater than the equivalent uncharged construct. In preferred embodiments the concentration of the charged constructs will be at least 7%, at least 10%, at least 12%, at least 15%, at least 17%, at least 20%, at least 23%, at least 25%, at least 27% or at least 30% greater than the equivalent uncharged construct. In particularly preferred embodiments the concentration of the charged constructs will be at least 35%, at least 40%, at least 45%, at least 50%, at least 55%, at least 60%, at least 70%, at least 75%, at least 80% or at least 90% greater than the equivalent uncharged construct. In yet other embodiments the concentration of the charged constructs will be at least 100%, at least 120%, at least 130%, at least 140%, at least 150%, at least 160%, at least 170%, at least 175%, at least 180%, at least 190% or at least 200% greater than the equivalent uncharged construct. In still other embodiments the concentration of the charged constructs will be at least 250%, at least 300%, at least 350%, at least 400%, at least 450%, or at least 500% greater than the equivalent uncharged construct.

It will be appreciated that this increase in purity and the advantages of the instant invention are applicable to a number of different multispecific constructs as the imposition of electrostatic charges may be applied selectively to encourage proper construct assembly. In this regard the methods disclosed herein are applicable to varied multivalent constructs (e.g., bivalent, trivalent, tetravalent, etc.) as well as multispecific constructs. By definition a multispecific construct will at least comprise a bivalent construct. As used herein, the term "valency" or the suffix "valent" refers to the number of potential antigen binding sites associated with an antibody. Each antigen binding site within an antibody binding region immunospecifically binds one determinant (e.g., an epitope on a cell surface protein). As shown by FIG. 6 depicting a tetravalent bispecific antibody, more than one binding site may bind to the same determinant. More generally, when an antibody comprises more than one antigen-binding site (multivalent), each antigen-binding site may immunospecifically bind the same or different determinants (e.g., may bind to different ligands or different antigens, or different epitopes or positions on the same antigen) provided that the construct ultimately reacts with at least two discrete determinants. In this respect it is important to note that the determinants may be on the same antigen (e.g., discrete epitopes or domains) or on separate antigens. Similarly, the determinants may be present on the same cell or may be present on different cells or different classes of cells.

Again it must be reiterated that the term "multispecific antibody" is used in the broadest sense and specifically covers an antibody comprising antigen-binding sites that has polydeterminant specificity (i.e., is capable of specifically binding to two, or more, different determinants on one biological molecule or is capable of specifically binding to discrete determinants on two, or more, different biological molecules). Such multispecific antibodies include, but are not limited to, full length antibodies, antibodies having two or more VL and VH domains, antibody fragments including a CL or CH1 region such as Fab, scFab bispecific diabodies and triabodies, and other compatible antibody fragments that have been linked covalently or non-covalently. In each case electrostatic charges may be appropriately distributed to selected antibody domains or regions to provide for the preferential assembly of the desired construct. For the purposes of the instant disclosure a "bispecific antibody" is a multispecific antibody comprising antigen-binding domains that are capable of specifically recognizing or binding to two different epitopes on one molecule or is capable of specifically recognizing or binding to epitopes on two different molecules. The bispecific antibody is also referred to herein as having "dual specificity" or as being "dual specific". See, for example, U.S.P.Ns. 2009/0130105, 2012/0121596, 2009/0155255 and 2011/0301331. Other compatible constructs may be found in U.S.P.N.s 2013/0017200, 2013/0004416 and 2012/0316324 as well as U.S. Pat. Nos. 8,349,332 and 7,521,056 as well as WO 2012/162583, WO 2013/005194, WO 94/04690 and WO 96/27011; Suresh et al., 1986, Methods in Enzymology, 121:210; Coloma, M. J., et al., Nature Biotech 15 (1997) 159-163; WO 2001/077342; and Morrison, S. L., Nature Biotech 25 (2007) 1233-1234 each of which is incorporated herein by reference.

In the context of the instant invention any art-recognized bispecific or multispecific construct, preferably comprising CH1 and CL domains and comprising a binding site recognizing a first determinant (e.g., epitope) and at least a second binding site that recognizes a second determinant which is distinct from the first determinant is compatible and may be assembled in conjunction with the teachings herein. In preferred embodiments the invention provides for bispecific antibodies in which two different antigen-binding sites are incorporated into a single molecule. Bispecific antibodies may be prepared by chemical cross-linking (Brennan, et al., Science 229, 81 (1985); Raso, et al., J. Biol. Chem. 272, 27623 (1997)), disulfide exchange, production of hybrid-hybridomas (quadromas), by transcription and translation to produce a single polypeptide chain embodying a bispecific antibody, or by transcription and translation to produce more than one polypeptide chain that can associate covalently to produce a bispecific antibody. The contemplated bispecific antibody can also be made entirely by chemical synthesis. The bispecific antibody may comprise two different variable regions, two different constant regions, a variable region and a constant region, or other variations. In each case the selective imposition of electrostatic charges may provide for preferential assembly of the desired construct and improved yields of the same.

III. Antibody Structure and Characteristics

As will be discussed in detail below and in the appended Examples, monospecific antibodies used to fabricate the multispecific constructs of the instant invention may be obtained from a variety of sources. By way of example such "source" antibodies may be generated using conventional immunization and hybridoma techniques or obtained from animals engineered to provide fully The following discussion is directed to the general structure, characteristics and sources of antibodies that may be used in conjunction with the teachings herein to provide the disclosed multispecific antibody constructs. It will be appreciated that the structures and properties of these "source antibodies" will, to a greater or lesser extent, be incorporated in the disclosed multispecific antibodies. By way of example if a source antibody is humanized to make it relatively less immunogenic it is likely that a multispecific antibody comprising all or part of the humanized source antibody will prove to be relatively less immunogenic. Similarly, if a source antibody is determined to be an internalizing antibody it is likely that a multispecific construct of the instant invention comprising all or part of such an antibody will found to internalize upon administration. Accordingly, the following discussion of antibody structures and characteristics are applicable to both the source antibodies and to the multispecific antibodies of the instant invention.

1. Antibody Structure

Antibodies and variants and derivatives thereof, including accepted nomenclature and numbering systems, have been extensively described, for example, in Abbas et al. (2010), Cellular and Molecular Immunology ($6^{th}$ Ed.), W.B. Saunders Company; or Murphey et al. (2011), Janeway's Immunobiology ($8^{th}$ Ed.), Garland Science.

An "antibody" or "intact antibody" typically refers to a Y-shaped tetrameric protein comprising two heavy (H) and two light (L) polypeptide chains held together by covalent disulfide bonds and non-covalent interactions. Human light chains comprise a variable domain (VL) and a constant domain (CL) wherein the constant domain may be readily classified as kappa or lambda based on amino acid sequence. Each heavy chain comprises one variable domain (VH) and a constant region, which in the case of IgG, IgA, and IgD, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (generally from about 10 to about 60 amino acids in IgG). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues.

As used herein the term "antibody" may be construed broadly and includes polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof, immunospecific antibody fragments such as Fd, Fab, F(ab')$_2$, F(ab') fragments, single-chain fragments (e.g. ScFv and ScFvFc); and derivatives thereof including Fc fusions and other modifications, and any other immunoreactive molecule so long as it exhibits preferential association or binding with a determinant.

The variable domains of antibodies show considerable variation in amino acid composition from one antibody to another and are primarily responsible for antigen recognition and binding. Variable regions of each light/heavy chain pair form the antibody binding site such that an intact IgG antibody has two binding sites (i.e. it is bivalent). VH and VL domains comprise three regions of extreme variability, which are termed hypervariable regions, or more commonly, complementarity-determining regions (CDRs), framed and separated by four less variable regions known as framework regions (FRs). The non-covalent association between the VH and the VL region forms the Fv fragment (for "fragment variable") which contains one of the two antigen-binding sites of the antibody. ScFv fragments (for single chain fragment variable), which can be obtained by genetic engineering, associates in a single polypeptide chain, the VH and the VL region of an antibody, separated by a peptide linker.

As used herein, the assignment of amino acids to each domain, framework region and CDR may be in accordance with one of the numbering schemes provided by Kabat et al. (1991) *Sequences of Proteins of Immunological Interest* (5$^{th}$ Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies*, 3$^{rd}$ Ed., Wily-VCH Verlag GmbH and Co. unless otherwise noted. The amino acid residues which comprise CDRs as defined by Kabat, Chothia and MacCallum as obtained from the Abysis website database (infra.) are set out in Table 1 below

TABLE 1

IDENTIFICATION OF CDR RESIDUES

|  | Kabat | Chothia | MacCallum |
| --- | --- | --- | --- |
| VH CDR1 | 31-35 | 26-32 | 30-35 |
| VH CDR2 | 50-65 | 52-56 | 47-58 |
| VH CDR3 | 95-102 | 95-102 | 93-101 |
| VL CDR1 | 24-34 | 24-34 | 30-36 |
| VL CDR2 | 50-56 | 50-56 | 46-55 |
| VL CDR3 | 89-97 | 89-97 | 89-96 |

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, N.Y., 2001 and Dinarello et al., Current Protocols in Immunology, John Wiley and Sons Inc., Hoboken, N.J., 2000. Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains. In: Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. Unless otherwise indicated, all CDRs set forth herein are derived according to the Abysis database website as per Kabat.

For heavy chain constant region amino acid positions discussed in the invention, numbering is according to the Eu index first described in Edelman et al., 1969, Proc, Natl. Acad. Sci. USA 63(1): 78-85 describing the amino acid sequence of myeloma protein Eu, which reportedly was the first human IgG1 sequenced. The Eu index of Edelman is also set forth in Kabat et al., 1991 (supra.). Thus, the terms "EU index as set forth in Kabat" or "EU index of Kabat" in the context of the heavy chain refers to the residue numbering system based on the human IgG1 Eu antibody of Edelman et al. as set forth in Kabat et al., 1991 (supra.). The numbering system used for the light chain constant region amino acid sequence is similarly set forth in Kabat et al., 1991.

The multispecific antibodies or immunoglobulins of the invention may be fabricated from an antibody that specifically binds, recognizes or associates with any relevant determinant. As used herein "determinant" means any immunospecifically detectable trait, property, marker or factor that is identifiably associated with, or specifically found in or on a particular cell, cell population, tissue or protein. Determinants may be morphological, functional or biochemical in nature and are preferably phenotypic. In certain preferred embodiments a determinant comprises a peptide or protein that is differentially expressed (over- or under-expressed) by specific cell types or by cells under certain conditions (e.g., during specific points of the cell cycle or cells in a particular niche). In such cases the determinant may comprise an epitope presented by the cell, protein or peptide. For the purposes of the instant invention a determinant preferably is differentially expressed on aberrant cancer cells and may be found on CD324 or Nectin-4 protein, or any of their splice variants, isoforms or family members, or specific domains, regions or epitopes thereof. An "immunogenic determinant", "antigenic determinant" means any protein or any fragment, region, domain or epitope thereof that can stimulate an immune response when introduced into an immunocompetent animal and is recognized by the antibodies produced from the immune response.

Selected embodiments of the invention comprise constructs incorporating monospecific "source" antibodies, or fragments thereof, that immunospecifically bind to either CD324 or Nectin-4. As previously discussed a "source" antibody comprises any monospecific antibody or fragment thereof that may be incorporated in a multispecific antibody of the instant invention using standard molecular biology or biochemical techniques while retaining desired binding characteristics. In certain embodiments, multispecific antibodies contemplated by the invention can be derived from such "source" antibodies through optional modification of the constant region or the epitope-binding amino acid sequences of the source antibody. In one embodiment a multispecific antibody can be derived from such source antibodies (e.g. an antibody that is bispecific and capable of binding to CD324 and Nectin-4 simultaneously). In other embodiments a multispecific antibody is "derived" from a source antibody by altering, deleting or replacing selected amino acids in the source antibody through mutation, substitution, integration, depletion or combinations thereof. In yet other embodiments, a "derived" antibody is one in which fragments of the source antibody (e.g., one or more CDRs) are combined with or incorporated into an acceptor antibody sequence to provide the derivative antibody (e.g. chimeric or humanized multispecific antibodies). These "derived" (e.g. humanized or CDR-grafted) multispecific antibodies can be generated using standard molecular biological techniques for various reasons such as, for example, to improve affinity for the determinant; to improve production and yield in cell culture; to reduce immunogenicity in vivo; to reduce toxicity or to facilitate conjugation of an active moiety or cytotoxin. Such antibodies may also be derived from source antibodies or multispecific constructs through modification of the mature molecule (e.g., glycosylation patterns or pegylation) by chemical means or post-translational modification.

2. Antibody Generation and Production

Source antibodies compatible with the invention can be produced using a variety of methods known in the art.

A. Production of Polyclonal Antibodies in Host Animals

The production of polyclonal antibodies in various host animals is well known in the art (see for example, Harlow and Lane (Eds.) (1988) Antibodies: A Laboratory Manual, CSH Press; and Harlow et al. (1989) Antibodies, NY, Cold Spring Harbor Press). In order to generate polyclonal antibodies, an immunocompetent animal is immunized with an antigenic determinant (e.g., a peptide or protein) or cells or preparations comprising an antigenic determinant. After a period of time, polyclonal antibody-containing serum is obtained by bleeding or sacrificing the animal. The serum may be used in the form obtained from the animal or the antibodies may be partially or fully purified to provide homogeneous source antibody preparations.

Any form of antigen, or cells or preparations containing the antigen, can be used to generate an antibody that is specific for a determinant. The term "antigen" is used in a broad sense and may comprise any immunogenic fragment or determinant of the selected target including a single epitope, multiple epitopes, single or multiple domains or the extracellular domain (ECD). The antigen may be an isolated full-length protein, a cell surface protein (e.g., immunizing with cells expressing at least a portion of the antigen on their surface), or a soluble protein (e.g., immunizing with only the ECD portion of the protein). The antigen may be produced in a genetically modified cell. Any of the aforementioned antigens may be used alone or in combination with one or more immunogenicity enhancing adjuvants known in the art. DNA encoding the antigen may be genomic or non-genomic (e.g., cDNA) and may preferably encode at least a portion of an ECD sufficient to elicit an immunogenic response. Any genetic vectors may be employed to transform the cells in which the antigen is expressed, including but not limited to adenoviral vectors, lentiviral vectors, plasmids, and non-viral vectors, such as cationic lipids.

B. Monoclonal Antibodies

In one embodiment, the invention contemplates use of monoclonal antibodies. As known in the art, the term "monoclonal antibody" or "mAb" refers to an antibody obtained from a population of substantially homogeneous antibodies, i.e., the individual antibodies comprising the population are identical except for possible mutations (e.g., naturally occurring mutations), that may be present in minor amounts.

Monoclonal antibodies can be prepared using a wide variety of techniques known in the art including hybridoma, recombinant engineering, phage display technologies, transgenic animals (e.g., a XenoMouse®) or some combination thereof. For example, monoclonal antibodies can be produced using hybridoma and biochemical and genetic engineering techniques such as described in more detail in An, Zhigiang (ed.) *Therapeutic Monoclonal Antibodies: From Bench to Clinic*, John Wiley and Sons, $1^{st}$ ed. 2009; Shire et. al. (eds.) *Current Trends in Monoclonal Antibody Development and Manufacturing*, Springer Science+Business Media LLC, $1^{st}$ ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981). In such techniques appropriate genetic material is isolated from cells producing the desired source antibody (e.g., screened hybridoma cells) and manipulated using art known techniques. Following production of multiple monoclonal antibodies that immunospecifically bind to a selected determinant, a particularly effective antibody may be selected through various screening processes, based on, for example, its affinity for the determinant.

C. Chimeric and Humanized Antibodies

In other embodiments, the multispecific antibodies of the invention may comprise chimeric antibodies derived from covalently joined protein segments derived from at least two different species (e.g., murine and human) or classes of antibodies. The term "chimeric" is directed to constructs in which a portion of the heavy and/or light chain is identical or homologous to corresponding sequences in antibodies derived from a particular species or belonging to a particular antibody class or subclass, while the remainder of the chain(s) is identical or homologous to corresponding sequences in antibodies derived from another species or belonging to another antibody class or subclass, as well as fragments of such antibodies (U.S. Pat. No. 4,816,567; Morrison et al., 1984, PMID: 6436822).

In one embodiment, a chimeric multispecific antibody may comprise murine VH and VL amino acid sequences and constant regions derived from human sources, for example, humanized antibodies as described below. In some embodiments, the antibodies can be "CDR-grafted", where the antibody comprises one or more CDRs from a particular species or belonging to a particular antibody class or subclass, while the remainder of the antibody chain(s) is/are identical with or homologous to a corresponding sequence in antibodies derived from another species or belonging to another antibody class or subclass. For use in humans, selected rodent CDRs, e.g., mouse CDRs may be grafted into a human antibody, replacing one or more of the naturally occurring CDRs of the human antibody. These constructs generally have the advantages of providing full strength antibody functions, e.g., complement dependent cytotoxicity (CDC) and antibody-dependent cell-mediated cytotoxicity (ADCC) while reducing unwanted immune responses to the antibody by the subject.

Similar to the CDR-grafted antibody is a "humanized" antibody. As used herein, "humanized" forms of non-human (e.g., murine) antibodies are chimeric antibodies that comprise amino acid sequences derived from one or more non-human immunoglobulins. In one embodiment, a humanized antibody is a human immunoglobulin (recipient or acceptor antibody) in which residues from a CDR of the recipient are replaced by residues from one or more CDRs of a non-human species (donor antibody) such as mouse, rat, rabbit, or non-human primate. A CDR grafted antibody may be a humanized antibody if a human receptor antibody is employed. In certain preferred embodiments, residues in one or more FRs in the heavy or light variable domains of the human immunoglobulin are replaced by corresponding non-human residues from the donor antibody to help maintain the appropriate three-dimensional configuration of the grafted CDR(s) and thereby improve affinity. This can be referred to as the introduction of "back mutations". Furthermore, humanized antibodies may comprise residues that are not found in the recipient antibody or in the donor antibody to, for example, further refine antibody performance.

Various sources can be used to determine which human sequences to use in the humanized antibodies. Such sources include human germline sequences that are disclosed, for example, in Tomlinson, I. A. et al. (1992) *J. Mol. Biol.* 227:776-798; Cook, G. P. et al. (1995) *Immunol. Today* 16: 237-242; Chothia, D. et al. (1992) *J. Mol. Biol.* 227:799-817; and Tomlinson et al. (1995) *EMBO J* 14:4628-4638; the V-BASE directory (VBASE2—Retter et al., Nucleic Acid Res. 33; 671-674, 2005) which provides a comprehensive directory of human immunoglobulin variable region sequences (compiled by Tomlinson, I. A. et al. MRC Centre for Protein Engineering, Cambridge, UK); or consensus human FRs described, for example, in U.S. Pat. No. 6,300,064.

CDR grafting and humanized source antibodies are described, for example, in U.S. Pat. Nos. 6,180,370 and 5,693,762. For further details, see, e.g., Jones et al., 1986, PMID: 3713831); and U.S. Pat. Nos. 6,982,321 and 7,087,409.

Another method is termed "humaneering" which is described, for example, in U.S.P.N. 2005/0008625. In another embodiment a non-human antibody may be modified by specific deletion of human T-cell epitopes or "deimmunization" by the methods disclosed in WO 98/52976 and WO 00/34317.

In selected embodiments at least 60%, 65%, 70%, 75%, or 80% of the humanized or CDR grafted source antibody heavy or light chain variable region amino acid residues will correspond to those of the recipient human sequences. In other embodiments at least 83%, 85%, 87% or 90% of the humanized source antibody variable region residues will correspond to those of the recipient human sequences. In a further preferred embodiment, greater than 95% of each of the humanized source antibody variable region residues will correspond to those of the recipient human sequences.

D. Human Antibodies

In another embodiment, source antibodies may comprise fully human antibodies. The term "human antibody" refers to an antibody which possesses an amino acid sequence that corresponds to that of an antibody naturally produced by a human and/or has been made using any of the techniques for making human antibodies described below.

Human source antibodies can be produced using various techniques known in the art. In one embodiment, recombinant human antibodies may be isolated by screening a recombinant combinatorial antibody library prepared using phage display. In one embodiment, the library is a scFv phage or yeast display library, generated using human VL and VH cDNAs prepared from mRNA isolated from B-cells.

Human source antibodies can also be made by introducing human immunoglobulin loci into transgenic animals, e.g., mice in which the endogenous immunoglobulin genes have been partially or completely inactivated and human immunoglobulin genes have been introduced. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and U.S. Pat. Nos. 6,075,181 and 6,150,584 regarding XenoMouse® technology; and Lonberg and Huszar, 1995, PMID: 7494109). Alternatively, a human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boerner et al., 1991, PMID: 2051030; and U.S. Pat. No. 5,750,373.

E. Recombinant Production of Antibodies

Source antibodies and fragments thereof, as well as the constructs of the instant invention may be produced or modified using genetic material obtained from antibody producing cells and recombinant engineering (see, for example, Berger and Kimmel, Guide to Molecular Cloning Techniques, Methods in Enzymology vol. 152 Academic Press, Inc., San Diego, Calif.; Sambrook and Russell (Eds.) (2000) *Molecular Cloning: A Laboratory Manual* ($3^{rd}$ Ed.), NY, Cold Spring Harbor Laboratory Press; Ausubel et al. (2002) *Short Protocols in Molecular Biology: A Compendium of Methods from Current Protocols in Molecular Biology*, Wiley, John & Sons, Inc.; and U.S. Pat. No. 7,709,611). The invention comprises charged multispecific antibodies and fragments thereof and the nucleic acids encoding said antibodies. The term "nucleic acid", as used herein, includes genomic DNA, cDNA, RNA and artificial variants thereof, whether single-stranded or double-stranded. More specifically the present invention comprises isolated nucleic acids, which may be modified to provide polypeptides having desired electrostatic properties, can be used to clone constant and variable region sequences for the manufacture of recombinant multispecific antibodies. The instant invention further provides vectors comprising such nucleic acids, which may be operably linked to a promoter (see, e.g., WO 86/05807; WO 89/01036; and U.S. Pat. No. 5,122,464); and other transcriptional regulatory and processing control elements of the eukaryotic secretory pathway. In addition the invention also provides prokaryotic and eukaryotic host cells comprising such vectors and host-expression systems.

As used herein, the term "host-expression system" includes any kind of cellular system which can be engineered to generate either the nucleic acids or the polypeptides and multispecific antibodies of the invention. Such host-expression systems include, but are not limited to microorganisms (e.g., *E. coli* or *B. subtilis*) transformed or transfected with recombinant bacteriophage DNA or plasmid DNA; yeast (e.g., *Saccharomyces*) transfected with recombinant yeast expression vectors; or mammalian cells (e.g., COS, CHO-S, HEK-293T, 3T3 cells) harboring recombinant expression constructs containing promoters derived from the genome of mammalian cells or viruses (e.g., the adenovirus late promoter). The host cell may be co-transfected with two expression vectors, for example, the first vector encoding a heavy chain derived polypeptide and the second vector encoding a light chain derived polypeptide.

Methods of transforming mammalian cells are well known in the art. See, for example, U.S. Pat. Nos. 4,399,216, 4,912,040, 4,740,461, and 4,959,455. The host cell may also be engineered to allow the production of an antigen binding molecule with various characteristics (e.g. modified glycoforms or multispecific antibodies having GnTIII activity).

For long-term, high-yield production of recombinant proteins stable expression is preferred. Accordingly, cell lines that stably express the selected multispecific antibody components may be engineered using standard art recognized techniques and form part of the invention. Rather than using expression vectors that contain viral origins of replication, host cells can be transformed with DNA controlled by appropriate expression control elements (e.g., promoter or enhancer sequences, transcription terminators, polyadenylation sites, etc.), and a selectable marker. Any of the selection systems well known in the art may be used, including the glutamine synthetase gene expression system (the GS system) which provides an efficient approach for enhancing expression under certain conditions. The GS system is discussed in whole or part in connection with EP 0 216 846, EP 0 256 055, EP 0 323 997 and EP 0 338 841 and U.S. Pat. Nos. 5,591,639 and 5,879,936. Another preferred expression system for the development of stable cell lines is the Freedom™ CHO-S Kit (Life Technologies).

Once an antibody of the invention has been produced by recombinant expression or any other of the disclosed techniques and secreted and assembled, it may be purified or isolated by methods known in the art, meaning that it is identified and separated and/or recovered from its natural environment and separated from contaminants that would interfere with diagnostic or therapeutic uses for the antibody. Isolated antibodies include antibodies in situ within recombinant cells.

These isolated preparations may be purified using various art recognized techniques, such as, for example, ion exchange and size exclusion chromatography, dialysis, diafiltration, and affinity chromatography, particularly Protein A or Protein G affinity chromatography.

F. Post-Production Selection

No matter how obtained, antibody-producing cells (e.g., hybridomas, yeast colonies, etc.) may be selected, cloned and further screened for desirable characteristics including, for example, robust growth, high antibody production and desirable antibody characteristics such as high affinity for the antigen of interest. Hybridomas can be expanded in vitro in cell culture or in vivo in syngeneic immunocompromised animals. Methods of selecting, cloning and expanding hybridomas and/or colonies are well known to those of ordinary skill in the art. Once the desired source antibodies are identified relevant genetic material may be isolated, manipulated and expressed using common, art-recognized molecular biology and biochemical techniques to provide the multispecific antibodies of the instant invention.

For examples source antibodies produced by naïve libraries (either natural or synthetic) may be of moderate affinity ($K_a$ of about $10^6$ to $10^7$ $M^{-1}$). To enhance affinity, affinity maturation may be mimicked in vitro by constructing antibody libraries (e.g., by introducing random mutations in vitro by using error-prone polymerase) and reselecting antibodies with high affinity for the antigen from those secondary libraries (e.g. by using phage or yeast display). WO 9607754 describes a method for inducing mutagenesis in a CDR of an immunoglobulin light chain to create a library of light chain genes.

Various techniques can be used to select source or multispecific antibodies, including but not limited to, phage or yeast display in which a library of human combinatorial antibodies or scFv fragments is synthesized on phages or yeast, the library is screened with the antigen of interest or an antibody-binding portion thereof, and the phage or yeast that binds the antigen is isolated, from which one may obtain the antibodies or immunoreactive fragments (Vaughan et al., 1996, PMID: 9630891; Sheets et al., 1998, PMID: 9600934; Boder et al., 1997, PMID: 9181578; Pepper et al., 2008, PMID: 18336206). Kits for generating phage or yeast display libraries are commercially available. There also are other methods and reagents that can be used in generating and screening antibody display libraries (see U.S. Pat. No. 5,223,409; WO 92/18619, WO 91/17271, WO 92/20791, WO 92/15679, WO 93/01288, WO 92/01047, WO 92/09690; and Barbas et al., 1991, PMID: 1896445). Such techniques advantageously allow for the screening of large numbers of candidate antibodies and provide for relatively easy manipulation of sequences (e.g., by recombinant shuffling).

3. Antibody Characteristics

Antibodies The disclosed multispecific antibodies may exhibit certain characteristics, which may be screened for; imparted by immunizing the antibody-producing animal with a particular antigen; or engineered through recombinant genetic techniques as described above, to enhance or refine certain desirable characteristics such as affinity, pharmacokinetics, safety profile etc.

A. Internalizing, Antagonist and Depleting Antibodies

In particularly preferred embodiments the multispecific antibodies of the inventions may comprise internalizing antibodies such that the antibody will bind to a determinant and will be internalized (along with any conjugated pharmaceutically active moiety) into an aberrant cell including tumor cells. Internalization may occur in vitro or in vivo. For therapeutic applications, internalization will preferably occur in vivo in a subject in need thereof. The number of antibody molecules internalized may be sufficient to kill an antigen-expressing cell. Depending on the potency of the antibody or, in some instances, antibody drug conjugate, the uptake of a single antibody molecule into the cell may be sufficient to kill the target cell to which the antibody binds. Whether an antibody internalizes upon binding to a mammalian cell can be determined by various assays including those described in U.S. Pat. No. 7,619,068.

In other selected embodiments the antibodies of the invention may be "antagonists" or "neutralizing" antibodies, meaning that the antibody may associate with a determinant and block or inhibit the activities of said determinant either directly or by preventing association of the determinant with a binding partner such as a ligand or a receptor, thereby interrupting the biological response that otherwise would result from the interaction of the molecules. A neutralizing or antagonist antibody will substantially inhibit binding of the determinant to its ligand or substrate when an excess of antibody reduces the quantity of binding partner bound to the determinant by at least about 20%, 30%, 40%, 50%, 60%, 70%, 80%, 85%, 90%, 95%, 97%, 99% or more as measured, for example, by target molecule activity or in an in vitro competitive binding assay. It will be appreciated that the modified activity may be measured directly using art recognized techniques or may be measured by the impact the altered activity has downstream (e.g., oncogenesis or cell survival).

In a further embodiment the antibodies or antibody drug conjugates disclosed herein will be "depleting" antibodies, meaning that the antibody will associate with a determinant on or near a cell surface and will induce the death or elimination of the cell (e.g., by CDC, ADCC or introduction of a cytotoxic agent). Preferably a depleting antibody will be able to incapacitate or eliminate at least 20%, 30%, 40%, 50%, 60%, 70%, 80%, 85%, 90%, 95%, 97%, or 99% of cells expressing a determinant in a defined cell population, e.g. CD324 and/or Nectin-4 expressing tumor cells. In some embodiments the cell population may comprise isolated tumor cells. In other embodiments the cell population may comprise whole tumor samples or heterogeneous tumor extracts. Standard biochemical techniques may be used to monitor and quantify the depletion of tumor cells.

B. Binding Affinity

Disclosed herein are multispecific antibodies that have a high binding affinity for a specific determinant(s) e.g. CD324 or Nectin-4. The term "$K_D$" refers to the dissociation constant or apparent affinity of a particular antibody-antigen interaction. An antibody of the invention can immunospecifically bind its target antigen when the dissociation constant $K_D$ ($k_{off}/k_{on}$) is $\leq 10^{-7}$M. The antibody specifically binds antigen with high affinity when the $K_D$ is $\leq 5 \times 10^{-9}$ M, and with very high affinity when the $K_D$ is $\leq 5\lambda 10^{-10}$ M. In one embodiment of the invention, the antibody has a $K_D$ of $\leq 10^{-9}$ M and an off-rate of about $1 \times 10^{-4}$/sec. In one embodiment of the invention, the off-rate is $<1 \times 10^{-5}$/sec. In other embodiments of the invention, the antibodies will bind to a determinant with a $K_D$ of between about $10^{-7}$M and $10^{-10}$ M, and in yet another embodiment it will bind with a $K_D \leq 2\lambda 10^{-10}$ M. Still other selected embodiments of the invention comprise antibodies that have a $K_D$ ($k_{off}/k_{on}$) of less than $10^{-6}$ M, less than $5 \times 10^{-6}$M, less than $10^{-7}$M, less than $5 \times 10^{-7}$M, less than $10^{-8}$M, less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-11}$M, less than $10^{-12}$M, less than $5 \times 10^{-12}$M, less than $10^{-13}$ M, less than $5 \times 10^{-13}$M, less than $10^{-14}$M, less than $5 \times 10^{-14}$M, less than $10^{-15}$M or less than $5 \times 10^{-15}$ M.

In certain embodiments, an antibody of the invention that immunospecifically binds to a determinant may have an association rate constant or $k_{on}$ (or $k_a$) rate (antibody+ antigen $(Ag)^k_{on} \leftarrow$ antibody-Ag) of at least $10^5$ M$^{-1}$s$^{-1}$, at least $2 \times 10^5$ M$^{-1}$s$^{-1}$ at least $5 \times 10^5$ M$^{-1}$s$^{-1}$ at least $10^6$ M$^{-1}$s$^{-1}$, at least $5 \times 10^6$ M$^{-1}$s$^{-1}$, at least $10^7$ M$^{-1}$s$^{-1}$, at least $5 \times 10^7$ M$^{-1}$s$^{-1}$, or at least $10^8$ M$^{-1}$s$^{-1}$.

In another embodiment, an antibody of the invention that immunospecifically binds to a determinant(s) may have a disassociation rate constant or $k_{off}$ (or $k_d$) rate (antibody+ antigen $(Ag)^k_{off} \leftarrow$ antibody-Ag) of less than $10^{-1}$ s$^{-1}$, less than $5 \times 10^{-1}$s$^{-1}$, less than $10^{-2}$ s$^{-1}$, less than $5 \times 10^{-2}$ s$^{-1}$, less than $10^{-3}$ s$^{-1}$ less than $5 \times 10^{-3}$ s$^{-1}$, less than $10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$ less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$ or less than $10^{-10}$ s$^{-1}$.

Binding affinity may be determined using various techniques known in the art, for example, surface plasmon resonance e.g. Biacore (see Example below), bio-layer interferometry, dual polarization interferometry, static light scattering, dynamic light scattering, isothermal titration calorimetry, ELISA, analytical ultracentrifugation, and flow cytometry.

IV. Exemplary Source Antibodies

Whatever multispecific framework or structure is ultimately selected (and whatever constant region mutations are introduced) to fabricate the multispecific construct it will be appreciated that the selected antigen-binding sites may be chosen to bind or associate with any one of numerous target antigens and may be derived from available (commercially or otherwise) antibodies. That is, using standard molecular engineering techniques the constructs may be fabricated to incorporate the antigen-binding regions or CDRs from any antibody or reactive fragment for which the nucleic acid or amino acid sequence is known. In this regard the antigen-binding site may, in preferred embodiments, be obtained or derived from an antibody selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. Given that the constituent amino acid sequences are known for each of these antibodies it is well within the skill of the art to select one or more of these antibodies, or immunospecific fragments thereof, and incorporate the selected structure in compatible multispecific constructs as described herein.

In addition to incorporating known antibody binding domains it is well within the art to generate antibodies to a known antigen and engineer the resulting antigen-binding sites or derivatives thereof into compatible multispecific sequences. Particularly preferred embodiments of the instant invention will comprise an antigen-binding site(s) that recognizes (e.g., binds or associates with) an antigen selected from the group consisting of octamer-binding transcription factor 4 (OCT4), nanog homeobox (Nanog), signal transducer and activator of transcription 3 (STAT3), epithelial cell adhesion molecule (EPCAM), cluster of differentiation 24 (CD24), cluster of differentiation 34 (CD34), neuroblastoma 84 (NB84), NAD-binding component of TrK potassium transporter (TrkA), disialoganglioside (GD2), cluster of differentiation 133 (CD133), cluster of differentiation 20 (CD20), cluster of differentiation 56 (CD56), cluster of differentiation (CD29), B7 homolog 3 (B7H3), cluster of differentiation 46 (CD46), transferrin receptor, junctional adhesion molecule 3 (JAM3), carboxypeptidase M, oncostatin M, leucine rich repeat containing G protein-coupled receptor 5 (Lgr5), leucine rich repeat containing G protein-coupled receptor 6 (Lgr6), cadherin-2 isoform 2 (CD325), nectin cell adhesion molecule 4 (nectin-4), nestin, SRY-box 1 (Sox1), B-lymphoma Moloney murine leukemia virus insertion region-1 (Bmi-1), embryonic ectoderm development (eed), enhancer of zeste homolog 1 (easyh1), enhancer of zeste homolog 2 (easyh2), mesoderm/mesenchyme forkhead 2 (mf2), YY1 transcription factor (yy1), SWI/SNF related, matrix associated, actin dependent regulator of chromatin, subfamily a, member 3 (smarcA3), SWI/SNF related, matrix associated, actin dependent regulator of chromatin, subfamily a, member 5 (smarcA5), SWI/SNF related, matrix associated, actin dependent regulator of chromatin, subfamily d, member 3 (smarcD3), SWI/SNF related, matrix associated, actin dependent regulator of chromatin, subfamily e, member 1 (smarcE1), MLLT3, super elongation complex subunit (mllt3), delta like canonical Notch ligand 1 (DLL1), delta like canonical Notch ligand 4 (DLL4), frizzled class receptor 1 (FZD1), frizzled class receptor 2 (FZD2), frizzled class receptor 3 (FZD3), frizzled class receptor 4 (FZD4), frizzled class receptor 6 (FZD6), frizzled class receptor 7 (FZD7), frizzled class receptor 8 (FZD8), frizzled class receptor 9 (FZD9), frizzled class receptor 10 (FZD10), Wnt family member 2 (WNT2), Wnt family member 2B (WNT2B), Wnt family member 3 (WNT3), Wnt family member 5A (WNT5A), Wnt family member 10B (WNT10B), Wnt family member 16 (WNT16), AXIN1, B-cell CLL/lymphoma 9 (BCL9), MYC proto-oncogene, bHLH transcription factor (MYC), TCF4 transcription factor 4 (TCF4) solute carrier family 7 member 8 (SLC7A8), solute carrier family 44 member 4 (SLC44A4), interleukin 1 receptor accessory protein (IL1RAP), tumor endothelial marker 8 (TEM8), transmembrane protease serine 4 isoform 7 (TMPRSS4), mucin 16, cell surface associated (MUC16), G protein-coupled receptor class C group 5 member B (GPRC5B), solute carrier family 6 member 14 (SLC6A14), solute carrier family 4 member 11 (SLC4A11), phosphatidic acid phosphatase type 2C (PPAP2C), caveolin 1 (CAV1), caveolin 2 (CAV2), protein tyrosine phosphatase, non-receptor type 3 (PTPN3), ephrin receptor A1 (EPHA1), ephrin receptor A2 (EPHA2), ephrin receptor A3 (EPHA3), ephrin receptor A4 (EPHA4), ephrin receptor A5 (EPHA5), ephrin receptor A6 (EPHA6), ephrin receptor A7 (EPHA7), ephrin receptor A8 (EPHA8), ephrin receptor A9 (EPHA9), ephrin receptor B1 (EPHB1), ephrin receptor B2 (EPHB2), ephrin receptor B3 (EPHB3), ephrin receptor B4 (EPHB4), ephrin receptor B5 (EPHB5), ephrin receptor B6 (EPHB6), ephrin A1 (EFNA1), ephrin A2 (EFNA2), ephrin A3 (EFNA3), ephrin A5 (EFNA5), ephrin A6 (EFNA6), ephrin B1 (EFNB1), ephrin B2 (EFNB2), ephrin B3 (EFNB3), solute carrier family 1 member 1 (SLC1A1), C-X3-C motif chemokine ligand 1 (CX3CL1), adenosine A2a receptor (ADORA2A), myelin protein zero like 1 (MPZL1), FLJ10052, C4.4A, sphingosine 1-phosphate receptor 3 (EDG3), retinoic acid receptor responder 1 (RARRES1), prostate transmembrane protein, androgen induced 1 (TMEPAI), 6-pyruvoyl tetrahydrobiopterin synthase (PTS), carcinoembryonic antigen related cell adhesion molecule 5 (CEACAM5), carcinoembryonic antigen related cell adhesion molecule 6 (CEACAM6), nidogen 2 (NID2), STEAP family member 1 (STEAP), ATP binding cassette subfamily A member 3 (ABCA3), cysteine rich transmembrane BMP regulator 1 (CRIM1), interleukin 1 receptor type 1 (IL1R1), opsin 3 (OPN3), decay-accelerating factor (DAF), mucin 1, cell surface associated (MUC1), carboxypeptidase D (CPD), neuromuscular ataxia (NMA), ADAM metallopeptidase domain 9 (ADAM9), gap junction protein alpha 1 (GJA1), solute carrier family 19 member 2 (SLC19A2), ATP binding cassette subfamily A member 1 (ABCA1), protocadherin 7 (PCDH7), adenylate cyclase 9 (ADCY9), solute carrier family 39 member 1 (SLC39A1), NPC intracellular cholesterol transporter 1 (NPC1), ectonucleotide pyrophosphatase/phosphodiesterase 1 (ENPP1), tumor suppressor candidate 3 (N33), glycoprotein nmb (GPNMB), lymphocyte antigen 6 family member E (LY6E), cadherin EGF LAG seven-pass G-type receptor 1 (CELSR1), LDL receptor related protein 3 (LRP3), reactive oxygen species modulator 1 (C20orf52), TMEPAI, feline leukemia virus subgroup C cellular receptor 1 (FLVCR), protocadherin alpha 10 (PCDHA10), G-protein coupled receptor GPR54 (GPR54), transforming growth factor beta receptor 3 (TGFBR3), semaphorin 4B (SEMA4B), protocadherin beta-2 precursor (PCDHB2), ATP binding cassette subfamily G member 2 (ABCG2), cluster of differentiation 166 (CD166), alpha fetoprotein (AFP), bone morphogenetic protein 4 (BMP-4), β-catenin, cluster of Differentiation 2 (CD2), cluster of differentiation 3 (CD3), cluster of differentiation 9 (CD9), cluster of differentiation 14 (CD14), cluster of differentiation 31 (CD31), cluster of differentiation 38 CD38), cluster of differentiation 44 (CD44), cluster of differentiation 45 (CD45), cluster of differentiation 74 (CD74), cluster of differentiation 90 (CD90), C—X—C motif chemokine receptor 4 (CXCR4), decorin, APC down-regulated 1 (APCDD1), protein tyrosine kinase 7 (inactive) (PTK7), epidermal growth factor receptor (EGFR), cluster of differentiation 105 (CD105), cluster of differentiation 64 (CD64), cluster of differentiation 16 (CD16), cluster of differentiation 16a (CD16a), cluster of differentiation 16b (CD16b), glioma-associated oncogene 1 (GLI1), glioma-associated oncogene (GLI2), cluster of differentiation 49b (CD49b), cluster of differentiation 49e (CD49e) and cluster of differentiation 49f (CD49f). It will be appreciated that the antibodies of the instant invention may be fabricated to react with any combination of the aforementioned antigens or with one of these antigens and any other known antigen. In certain preferred embodiments the multispecific constructs may bind to two or more discrete determinants on any of these antigens. As shown in the appended Examples particularly preferred antibodies may be fabricated that bind to Nectin-4, CD234 or combinations thereof.

V. Uses of Multispecific Antibodies

1. Therapeutics

The present invention is directed to the fabrication and use of multispecific antibodies and antibody drug conjugates thereof for the diagnosis, theragnosis, treatment and/or prophylaxis of various disorders. In preferred embodiments, the bispecific antibodies of the current invention may be used to treat various proliferative or neoplastic disorders, including both solid tumors and hematologic malignancies, in subjects in need thereof. In this regard it will be appreciated that the disclosed antibodies may be administered alone or in conjunction with adjunct therapies such as chemotherapy or radiotherapy. While the "subject" or "patient" to be treated will be preferably human, as used herein the terms are expressly held to comprise any mammalian species.

Exemplary neoplastic or proliferative conditions subject to treatment in accordance with the instant invention may be benign or malignant; solid tumors or other blood neoplasia; and may be selected from the group including, but not limited to: adrenal gland tumors, AIDS-associated cancers, alveolar soft part sarcoma, astrocytic tumors, bladder cancer (squamous cell carcinoma and transitional cell carcinoma), blastocoelic disorders, bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, epithelial disorders, Ewing's tumors, extraskeletal myxoid chondrosarcoma, fibrogenesis imperfecta ossium, fibrous dysplasia of the bone, gallbladder and bile duct cancers, gastric cancer, gastrointestinal, gestational trophoblastic disease, germ cell tumors, glandular disorders, head and neck cancers, hypothalamic, intestinal cancer, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), macrophagal disorders, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, stromal disorders, synovial sarcoma, testicular cancer, thymic carcinoma, thymoma, thyroid metastatic cancer, and uterine cancers (carcinoma of the cervix, endometrial carcinoma, and leiomyoma).

In particularly preferred embodiments the antibodies of the instant invention will be used to treat a neoplastic disorder wherein the neoplastic disorder or cancer is selected from the group consisting of adrenal cancer, bladder cancer, cervical cancer, endometrial cancer, kidney cancer, liver cancer, lung cancer (small cell and non-small cell), ovarian cancer, colorectal cancer, pancreatic cancer, prostate cancer and breast cancer.

2. Diagnostics

In addition to therapeutic uses the present invention provides in vitro or in vivo methods for detecting, diagnosing or monitoring progression of proliferative disorders and methods of screening cells in or from a patient to identify tumorigenic cells. Such methods include identifying an individual having cancer for treatment or monitoring progression of a cancer comprising contacting the patient or a sample obtained from a patient (i.e. either in vivo or in vitro) with a multispecific antibody as described herein and detecting presence or absence, or level of association, of the cell bound antibody or free antigen molecules in the sample. In particularly preferred embodiments the antibody will comprise a detectable label or reporter molecule.

3. Antibody Drug Conjugates

In accordance with the teachings herein it will further be appreciated that the disclosed bispecific and multispecific constructs may be used in a conjugated (e.g., with a cytotoxic agent) or unconjugated state.

As indicated the antibodies of the invention may be conjugated with pharmaceutically active molecules (e.g., cytotoxins), diagnostic moieties or biocompatible modifiers (e.g., polyethylene glycol polymers). The term "conjugate" is used broadly and means the covalent or non-covalent association of any biologically active or detectable molecule or drug with the disclosed antibodies regardless of the method of association, resulting in the production of a so called "antibody-drug conjugate" (ADC). The resulting ADCs of the invention may be used for both therapeutic and diagnostic purposes.

An ADC can typically be represented by the formula: Ab-[L-D], where "Ab" is a multispecific antibody, "D" is preferably a therapeutic or diagnostic moiety, and "L" is a linker. While an "Ab" and a "D" moiety are both necessary components of an ADC, the presence of the "L" moiety is optional. The ADCs of the invention may comprise peptides, prodrugs which are metabolized to an active agent in vivo, polymers, nucleic acid molecules, small molecules, binding agents, mimetic agents, synthetic drugs, inorganic molecules, organic molecules and radioisotopes. In a preferred embodiment, the "Ab" is a bispecific antibody of the invention.

Several varieties or types of linkers may be used to associate the "Ab" moiety with the "D" moiety. In some embodiments, the linker is cleavable, whereas in other embodiments the linker is noncleavable. The selected antibodies can also be directly conjugated to radioisotopes or may comprise macrocyclic chelators useful for conjugating radiometal ions.

Multispecific antibodies of the present invention may be conjugated to various types of diagnostic or detectable agents, markers or reporters which may be, for example, a biological molecule (e.g., a peptide or nucleotide), small molecule, fluorophore, or radioisotope. Labeled antibodies can be useful for diagnosis and monitoring the development or progression of a proliferative disorder or as part of a clinical testing procedure to determine the efficacy of a particular therapy including the disclosed antibodies (i.e. theragnostics) or to determine a future course of treatment. Such markers or reporters may also be useful in purifying the selected modulator, antibody analytics (e.g., epitope binding or antibody binning), separating or isolating cancer cells or in preclinical procedures or toxicology studies.

Similarly multispecific antibodies of the present invention may also be conjugated to a "therapeutic moiety" or "drug" such as an anti-cancer agent including, but not limited to, cytotoxic agents, cytostatic agents, anti-angiogenic agents, debulking agents, chemotherapeutic agents, radiotherapy and radiotherapeutic agents, targeted anti-cancer agents, biological response modifiers, cancer vaccines, cytokines, hormone therapies, radiation therapy and anti-metastatic agents and immunotherapeutic VI. Pharmaceutical Preparations and Clinical Uses 1. Formulations and Routes of Administration Compositions of the invention may be formulated as desired using art recognized techniques. In some embodiments, the bispecific antibodies of the invention may be administered neat or with a minimum of additional components while others may optionally be formulated to contain suitable pharmaceutically acceptable carriers comprising excipients and auxiliaries that are well known in the art (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3rd ed., Pharmaceutical Press (2000)). Disclosed antibodies for systemic administration may be formulated for any type of administration including enteral, parenteral or topical administration.

The compounds and compositions of the invention may be administered in vivo, to a subject in need thereof, by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The appropriate formulation and route of administration may be selected according to the intended application and therapeutic regimen.

2. Combination Therapies

Combination therapy refers to the administration of an antibody of the invention and one or more active moieties including therapeutic moieties (e.g., anti-cancer agents.)

Combination therapies may be particularly useful in preventing or treating neoplastic cell proliferation, cancer, recurrence of cancer, or metastasis of cancer. The antibodies of the instant invention may function as sensitizing or chemosensitizing agents by reducing the tumorigenic cells that would otherwise support and perpetuate the tumor mass; and thereby allow for more effective use of current standard of care debulking or anti-cancer agents.

There is no requirement for the combined results to be additive of the effects observed when each treatment (e.g., antibody or anti-cancer agent) is conducted separately. Although additive effects are generally desirable, any increased anti-tumor effect above one of the single therapies is beneficial. Furthermore, the invention does not require the combined treatment to exhibit synergistic effects. However, those skilled in the art will appreciate that with certain selected combinations that comprise preferred embodiments, synergism may be observed.

In practicing combination therapy, the antibody (preferably in the form of an ADC) and therapeutic moiety may be administered to the subject simultaneously, either in a single composition, or as two or more distinct compositions using the same or different administration routes. Alternatively, treatment with the antibody may precede or follow the therapeutic moiety treatment by, e.g., intervals ranging from minutes to weeks. In one embodiment, both the therapeutic moiety and the antibody are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the antibody and the therapeutic moiety.

The combination therapy can be administered until the condition is treated, palliated or cured on various schedules such as once, twice or three times daily, once every two days, once every three days, once weekly, once every two weeks, once every month, once every two months, once every three months, once every six months, or may be administered continuously. The combination therapy can be administered via any route.

In one embodiment an antibody is administered in combination with one or more therapeutic moieties for short or long treatment cycles to a subject in need thereof. The invention contemplates discontinuous administration or daily doses divided into several partial administrations. The antibody and therapeutic moiety may be administered interchangeably, on alternate days or weeks; or a sequence of antibody treatments may be given, followed by one or more treatments with the therapeutic moiety.

In another embodiment the antibodies of the instant invention may be used in maintenance therapy to reduce or eliminate the chance of tumor recurrence following the initial presentation of the disease. Preferably the disorder will have been treated by antibodies of the invention or by other therapeutic agents and the initial tumor mass eliminated, reduced or otherwise ameliorated so the patient is asymptomatic or in remission. At such time the subject may be administered pharmaceutically effective amounts of the disclosed antibodies one or more times even though there is little or no indication of disease using standard diagnostic procedures. In some embodiments, the effectors will be administered on a regular schedule over a period of time, such as weekly, every two weeks, monthly, every six weeks, every two months, every three months every six months or annually. One skilled in the art could readily determine favorable dosages and dosing regimens to reduce the potential of disease recurrence. Such treatments could be continued for a period of weeks, months, years or even indefinitely depending on the patient response and clinical and diagnostic parameters.

In another embodiment the antibodies of the invention may be used prophylactically to prevent or reduce the possibility of tumor metastasis following a debulking procedure. As used in the instant disclosure a "debulking procedure" is defined broadly and means any procedure, technique or method that eliminates, reduces, treats or ameliorates a tumor or tumor proliferation. Exemplary debulking procedures include, but are not limited to, surgery, radiation treatments (i.e., beam radiation), chemotherapy, immunotherapy or ablation. The antibodies may be administered one or more times at pharmaceutically effective dosages as determined using standard techniques. Preferably the dosing regimen will be accompanied by appropriate diagnostic or monitoring techniques that allow it to be modified.

VII. Articles of Manufacture

Pharmaceutical packs and kits comprising one or more containers, comprising one or more doses of a composition of the invention are also provided. The doses of the composition of the invention may be supplied in any form, including but not limited to, a single-use prefilled syringe for injection or a lyophilized powder that may be reconstituted upon addition of an appropriate liquid. The composition may comprise any relevant additive.

VIII. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. As used in this specification and the appended claims, the singular forms "a," "an" and "the" include plural referents unless the context clearly dictates otherwise. In addition, ranges provided in the specification and appended claims include both end points and all points between the end points.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various references that are cited and discussed throughout the present specification unless otherwise indicated.

EXAMPLES

The present invention, thus generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1

Design of Constructs for Heavy Chain/Light Chain Pairing

Crystal structures of IgGs and Fab fragments were studied to identify candidate sites for residue substitutions to create specificity in pairing between two different heavy chains and two different light chains. Initial analysis was performed on the Protein Data Bank (PDB) model ID 2XRA, with confirmation of candidate site pairs on PDB model ID 3DVN. Candidate sets of residues were chosen on the CH1 and CL domains and are summarized in Table 2 and shown in FIG. 2. Residue numbering follows the Kabat numbering scheme, and one-letter amino acid abbreviations are used. H172 on CH1 was found to be in close proximity to two residues on the CL domain, S174 and N138, so both sites were chosen for residue substitutions. Additionally, H172 on CH1 could also potentially interact with N137 on CL.

Note that this analysis and subsequent multispecific constructs employ a kappa light chain for the purposes of demonstrating the concepts of the instant invention. In view of the instant disclosure the same analytical procedures could readily be applied to lambda light chains which could then be incorporated in the disclosed constructs without undue experimentation. Similarly, for the purposes of illustration an IgG1 heavy chain constant region was used for the subsequent analysis and incorporated in the resulting constructs. Again, one skilled in the art could readily incorporate other known heavy chain constant regions (e.g., IgG3) and use the disclosed techniques and principles to generate multispecific constructs in accordance with the instant invention.

TABLE 2

EXEMPLARY CH1 AND CL SITES FOR RESIDUE SUBSTITUTIONS

| Position # | CH1 residue | CL residue(s) |
|---|---|---|
| 1 | S188 | S176 |
| 2 | H172 | S174, N138 |
| 3 | T192 | N137 |
| 4 | H172 | N137 |

Residue substitutions to provide charged residues were effected in order to impart the desired electrostatic forces and thereby create selectivity for heavy chain/light chain pairing (thus leading to preferential assembly). Substitutions to arginine or lysine were used to create positive charge (though in other cases it may be possible to substitute histidine), while substitutions to aspartic acid or glutamic acid were used to create negative charge. For the purpose of evaluating the candidate mutations (described in detail in Example 2), residue substitutions were made using the Quikchange mutagenesis kit (Agilent) on an anti-CD324 antibody, hSC10.17 (termed "anti-CD324 antibody"; see USPN 2013/0058947). Substitutions were made at the sites described in Table 2 both alone and in combination. Each set of interacting residues is potentially mutually exclusive, so there could be differently charged residues on different sites of the heavy chain (e.g. S188K T192D on CH1), as long as charge-compatible substitutions are incorporated on the corresponding light chain (e.g. S176D N137K on corresponding CL) and charge-incompatible substitutions are incorporated on the non-corresponding light chain (e.g. S176K, N138D on non-corresponding CL). Therefore, heavy chain constructs contained the following CH1 residue substitutions and all of its combinations: S188$X_1$ H172$X_2$ T192$X_3$, where $X_1$, $X_2$ or $X_3$ could each be K, R, D, E or the wild type residue. Similarly, light chain constructs contained the following CL residue substitutions and all of its combinations: S174$X_1$ S174 $X_2$ N137$X_3$ N138$X_4$ where $X_1$, $X_2$, $X_3$, or $X_4$ could each be K, R, D, E or the wild type residue. It will be appreciated that the substitutions selected for one chain will dictate the substitutions on the corresponding chain. That is, if a positive charge is imparted to the heavy chain a negative charge will be imparted to the desired light chain partner (or a positive charge to an undesired light chain).

Example 2

Evaluation of Candidate CH1/CL Mutations

The exemplary bispecific antibody contained two different light chains and two different heavy chains with modifications in the Fc region for asymmetric heavy chain pairing. However, in order to simplify the screening of candidate CH1 and CL mutations, only one heavy chain and one light chain were tested at a time for assembly into a full IgG, without asymmetric heavy chain pairing. Candidate heavy and light chain constructs were cloned into pEE6.4HuIgG1 and pEE12.4Hu-kappa expression vectors (both from Lonza AG) with unmodified Fc regions. Plasmids containing heavy and light chains with candidate CH1 and CL mutations were co-transfected in HEK-293T cells using 293Fectin as a transfection reagent (Novagen). For each CH1 candidate mutation, co-transfections were performed in separate reactions using light chains containing mutations of both opposite and same charge at the corresponding CL site. For example the T192K heavy chain construct was co-transfected with light chain constructs with either N137K, N137R, N137D, or N137E mutations.

After two to three days, ELISA analysis was used to measure the assembly of full IgG. Goat anti-human Fc polyclonal antibody (Jackson Immunoresearch) was coated onto a high protein binding ELISA plate overnight in sodium bicarbonate buffer pH 8.0. The plate was then washed three times, and blocked with PBS+3% BSA+0.1% Tween. The plate was then washed three times and incubated with unpurified cell culture supernatants diluted in blocking buffer, followed by an additional three washes and incubation with horseradish peroxidase conjugated goat anti-human kappa light chain (Southern Biotech). The plate was then washed three times and developed using the 1-Step Turbo TMB reagent (Pierce) and quenched with 2 M sulfuric acid. The use of anti Fc capture and anti-kappa light chain detection allows for specific detection of fully assembled IgG.

Figure 3A:
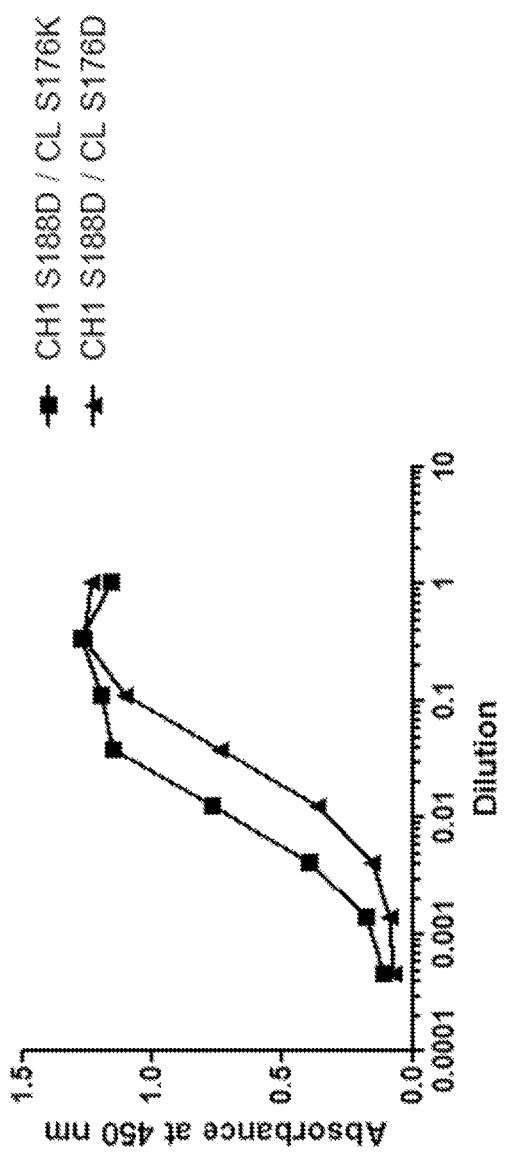
FIGS. 3A-3C show the results of representative ELISA assays used to screen candidate heavy and light chains with candidate mutations for full IgG assembly.

The comparison of full IgG assembly of pairs of oppositely charged residues with pairs of equivalently charged residues makes it possible to evaluate the likelihood of heavy chain/light chain mispairing. FIG. 3A shows a comparison of IgG assembly of the oppositely-charged pair, CH1 S188D/CL S176K, with the equivalently charged pair CH1 S188D/CL S176D. The CH1 S188D/CL S176K construct exhibited enhanced IgG assembly compared to the CH1 S188D/CL S176D construct, indicating that this site is energetically important for heavy chain/light chain pairing. Additionally, a heavy chain with CH1 S188D can disfavor the pairing with a light chain with CL S176D, and therefore, CL S176D is a candidate mutation for the light chain not corresponding to the heavy chain with CH1 S188D.

Figure 3B:
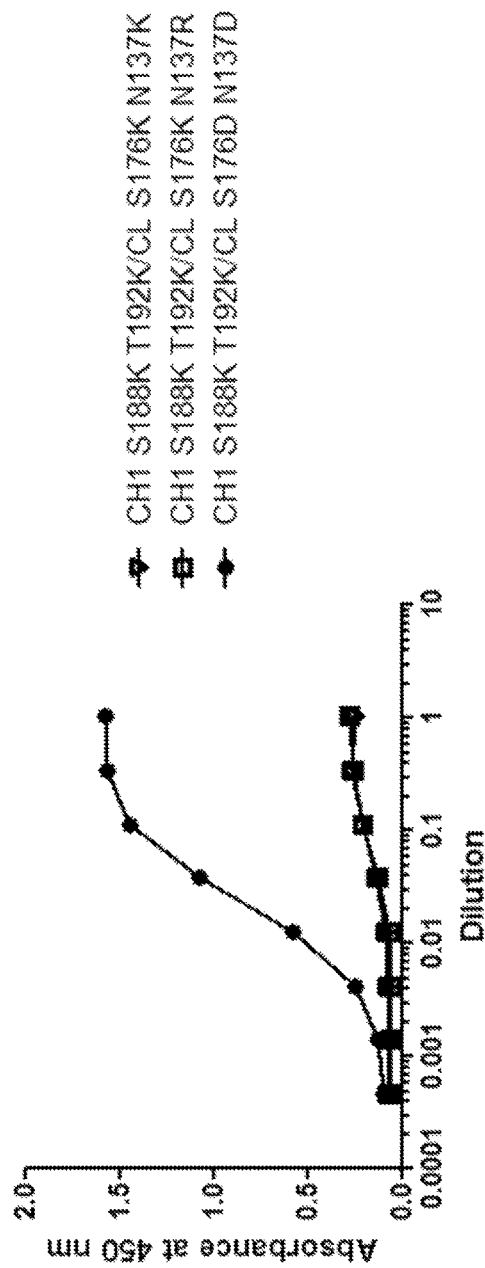
Figure 3C:
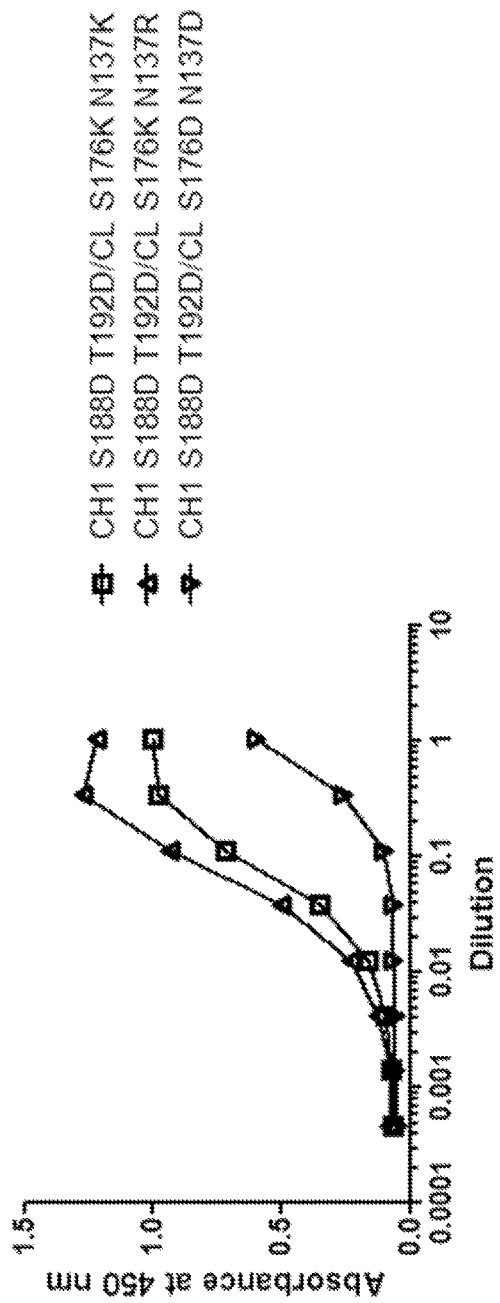

FIGS. 3B and 3C show examples of IgG assembly with a combination of residue substitutions on the CH1 and CL domains. (In FIG. 3B, two of the lines overlap.) In all cases, oppositely charged pairs have much better IgG assembly than equivalently charged pairs. Furthermore, when compared to the single mutations in FIG. 3A, the difference in IgG assembly, and thus, the selectivity in heavy chain/light chain pairing is significantly improved.

The results from the experiments provide an effective example on how to combine heavy and light chain mutations on the two arms of the IgG bispecific antibody. A light chain construct chosen for one arm must effectively assemble with the heavy chain construct for the same arm, while simultaneously ineffectively assemble with the heavy chain construct of the other arm. For example, based on the results shown in FIG. 3C, CH1 S188D T192D/CL S176K N137K can be used on one arm of a bispecific, while CH1 S188K T192K/CL S176D N137D can be used on another arm. The lack of IgG assembly of equivalently charged residues on both arms indicates that light chain with CL S176D N137D will not effectively pair with the heavy chain with CH1 S188D T192D, and vice versa.

Example 3

Generation of Bispecific Antibodies

The utility of the sites identified in Example 2 was evaluated in an IgG-like bispecific format such as the one shown in FIG. 1. Bispecific antibodies were constructed using variable regions from the anti-CD324 antibody hSC10.17 (see U.S.P.N. 2013/0058947), and Ha22-2(2,4) 6.1, which binds Nectin-4 (termed "anti-Nectin-4 antibody"; see U.S.P.N. 2012/0078028). The final bispecific antibody was termed anti-CD324/N4 antibody. Knob into holes ("KiH") with stabilizing disulfides were used for asymmetric heavy chain pairing (Merchant et al., supra). Knob into holes residue mutation numbering follows the EU numbering scheme. Selected CH1 and CL mutations from Example 2 were used in the CH1 and CL domains. All mutations were incorporated using the Quikchange Mutagenesis kit according to the manufacturer's instructions (Agilent). These mutations are summarized in Table 3. The first construct is an anti-CD324/N4 bispecific construct having a knob in hole mutation in the constant region of HC 1 and various mutations in the variable regions of the heavy and light chain as described in Example 1 above. The mutations for heavy chain/light chain pairing are mutually exclusive of the general strategy and specific mutations chosen for knob into holes asymmetric heavy chain pairing. For example, in heavy chain #1 of both constructs, S188D S192D is not required to be paired with T366W S354C.

TABLE 3

SELECTED MUTATIONS DRIVE THE FORMATION OF STABLE BISPECIFIC ANTIBODIES

| Construct | Chain | Variable Region Specificity | Mutations for Asymmetric HC Pairing (KiH) (EU numbering) | Mutations for HC/LC Pairing (Kabat Numbering) |
|---|---|---|---|---|
| Anti-CD324/N4 KiH-KK | HC 1 | CD324 | T366W S354C | S188D, T192D |
|  | HC 2 | Nectin 4 | T366S, L368A, Y407A, Y349C | S188K, T192K |
|  | LC 1 | CD324 |  | S176K, N137K |
|  | LC 2 | Nectin 4 |  | S176D, N137D |
| Anti-CD324/N4 KiH-KR | HC 1 | CD324 | T366W S354C | S188D, T192D |
|  | HC 2 | Nectin 4 | T366S, L368A, Y407A, Y349C | S188K, T192K |
|  | LC 1 | CD324 |  | S176K, N137R |
|  | LC 2 | Nectin 4 |  | S176D, N137D |

Bispecific antibodies were generated in transient transfections using art-recognized techniques of suspension or adherent cultures of HEK-293T cells, or suspension CHO-S cells. Polyethylenimine polymer was used as the transfecting reagent, and equal mass ratios of four expression vectors for each of the two heavy chains and two light chains were used for co-transfections. Seven to ten days after transfection, the bispecific antibodies were purified from clarified cell-supernatants using MabSelect SuRe™ Protein A (GE Healthcare Life Sciences). For the purposes of identification the multispecific antibody with the CD324 LC 1 mutation S176K, N137R is labeled "KR" (i.e., KiH-KR) while the multispecific antibody having the CD324 LC 1 mutation S176K, N137K is labeled "KK" (i.e., KiH-KK) in the instant specification and FIGS.

The bispecific antibodies were then characterized using (i) a bridging ELISA assay to confirm that the antibodies were able to bind specifically to both CD324 and Nectin-4 and; (ii) an in vitro killing assay to demonstrate the ability of the bispecific antibodies to internalize and mediate the delivery of a cytotoxin to live cells.

The bridging ELISA assay was performed by coating Nectin-4 protein (R&D Systems) onto an ELISA plate, which was then blocked with PBS+0.1% Tween and 3% BSA. The plate was incubated with either anti-CD324/N4 bispecific antibody, monospecific anti-Nectin-4 antibody or monospecific anti-CD324 antibody. After three washes with PBS+0.1% Tween, the plate was incubated with biotinylated CD324 protein with a tryptophan to alanine substitution at position 2. This substitution improves solubility and has no effect on binding of the anti-CD324 antibody. After three additional washes, the plate was incubated with horseradish peroxidase conjugated streptavidin. After three washes, the plates were developed using the 1-step Turbo TMB reagent (Pierce), and quenched with 2 M sulfuric acid. ELISA analysis indicated that all four bispecific constructs, shown in Table 3 above, were capable of bridging Nectin-4 and CD324, whereas each of the monospecific antibodies individually was not (data not shown). These results confirm that the bispecific constructs were assembled correctly and exhibit specificity to both Nectin-4 and CD324.

Example 4

In Vitro Characterization of Bispecific Antibodies

An in vitro killing assay was used to determine the ability of the bispecific antibodies generated in Example 3 to bind to their target antigen, internalize, and mediate the delivery of a cytotoxin to live cells. The assay uses antibodies that are linked to saporin and to a secondary antibody FAB fragment. Saporin is a plant toxin that deactivates ribosomes, thereby inhibiting protein synthesis and resulting in the death of the cell. Saporin is only cytotoxic inside the cell where it has access to ribosomes, but is unable to internalize on its own. Therefore, saporin-mediated cellular cytotoxicity in these assays is indicative of the ability of the FAB-Saporin antibody conjugate to internalize into the target cell only upon binding and internalization of the antibody.

Table 4 shows the results of an in vitro killing assay performed using three cell lines: MCF-7, which expresses both Nectin-4 and CD324; SKBR3, which expresses Nectin-4 only; and HEK-293T-hCD324, an engineered HEK-293T cell line that overexpresses CD324 and does not express Nectin-4. The HEK-293T-hCD324 cell line was made by transduction of HEK-293T cells using a bicistronic lentiviral vector expressing both human CD324 and GFP, and expansion of the $CD324^+$ FACS-sorted subset. 500 cells/well of MCF-7, SKBR3, or HEK-293T-hCD324 in DMEM supplemented with 10% fetal bovine serum were plated into 96 well tissue culture treated plates. After incubation for 24 hours, 2 nM anti-human IgG Fab fragment covalently linked to saporin (Advanced Targeting Systems) was combined with unlabeled anti-CD324/N4 bispecific antibodies or anti-CD324 or anti-Nectin-4 monospecific antibodies at concentrations varying between 0.01 pM and 1000 pM. The Fab-saporin-antibody complexes were added to the cells. The ability of the complexes to internalize and kill the cells was measured after 72, 96 or 144 hours by measuring cell viability of MCF-7, HEK-293T-hCD324 or SKBR3 cells, respectively, using Cell Titer Glo® (Promega) as per manufacturer's instructions. Raw luminescence counts using cultures containing cells exposed to the Fab-saporin fragment were set as 100% reference values and all other counts calculated accordingly (referred to as "Normalized RLU").

The results shown in Table 4 immediately below demonstrate that anti-CD324/N4 bispecific antibodies (as described in Table 3 above) were equally or more effective at delivering toxin as monospecific anti-CD324 or anti-Nectin-4 antibodies in the $CD324^+$ $Nectin-4^+$ cell line, MCF-7. The results also demonstrated that anti-$CD324^-$/$Nectin-4^+$ bispecific antibodies were able to deliver toxin in both the SKBR3 $CD324^-Nectin-4^+$ cell line, and the HEK-293T-hCD324 $CD324^+Nectin-4^-$ cell line, but were less effective at delivering toxin than either monospecific anti-Nectin-4 or anti-CD324 antibodies, respectively. These data support the finding that the bispecific antibodies generated in Example 3 were able to internalize and kill cells in vitro, with increased specificity to cell lines expressing both antigens, and with decreased off-target toxicity on single positive cells compared to monospecific antibodies.

TABLE 4

BISPECIFIC ANTIBODY IN VITRO EFFICACY

| | IC50 (pM) | | |
|---|---|---|---|
| | MCF-7 | SKBR3 | HEK-293T-hCD324 |
| Anti-Nectin-4 antibody | 9.94 | 0.95 | >1000 |
| Anti-CD324 antibody | 3.10 | >1000 | 0.27 |
| Anti-CD324/N4 KiH-KK | 5.98 | 144.1 | 12.25 |
| Anti-CD324/N4 KiH-KR | 5.21 | 77.8 | 5.66 |
| Human IgG1 | >1000 | >1000 | >1000 |

Example 5

Characterization of Bispecific Antibodies

The affinity of select antibodies for histidine tagged CD324 and Nectin-4 (RnD systems) protein was determined using surface plasmon resonance using a BIAcore 2000 (GE Healthcare). An anti-human antibody capture kit was used to immobilize the antibodies on a CM5 biosensor chip. Prior to each antigen injection cycle, 2 µg/mL of each of the anti-CD324/N4 bispecific antibodies or monospecific anti-CD324 or anti-Nectin-4 antibodies were captured on the surface with a contact time of 40 second and a flow rate of 5 µL/min. The captured antibody loading from baseline was constant at 130-140 response units. Following antibody capture and 1 minute baseline, monomeric CD324 or Nectin 4 antigens were flowed over the surface for a 2 minute association phase followed by a 4 minute dissociation phase at a flow rate of 10 µL/min. The anti-human antibody capture chip was regenerated with 30 second contact time of 3M magnesium chloride at 10 µL/minute following each cycle.

Figure 4A:
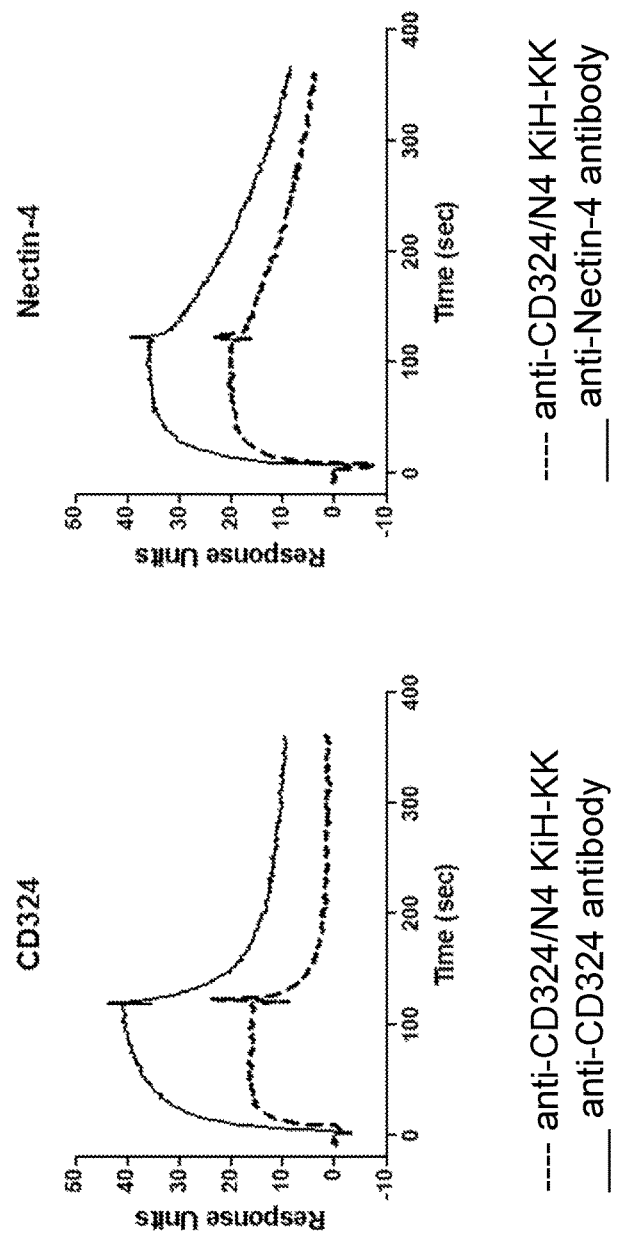
FIG. 4 shows Biacore curves for the bispecific and corresponding bivalent, monospecific IgGs. Bispecific curves are represented by dashed lines, while the control antibody is represented by solid lines.
Figure 4B:
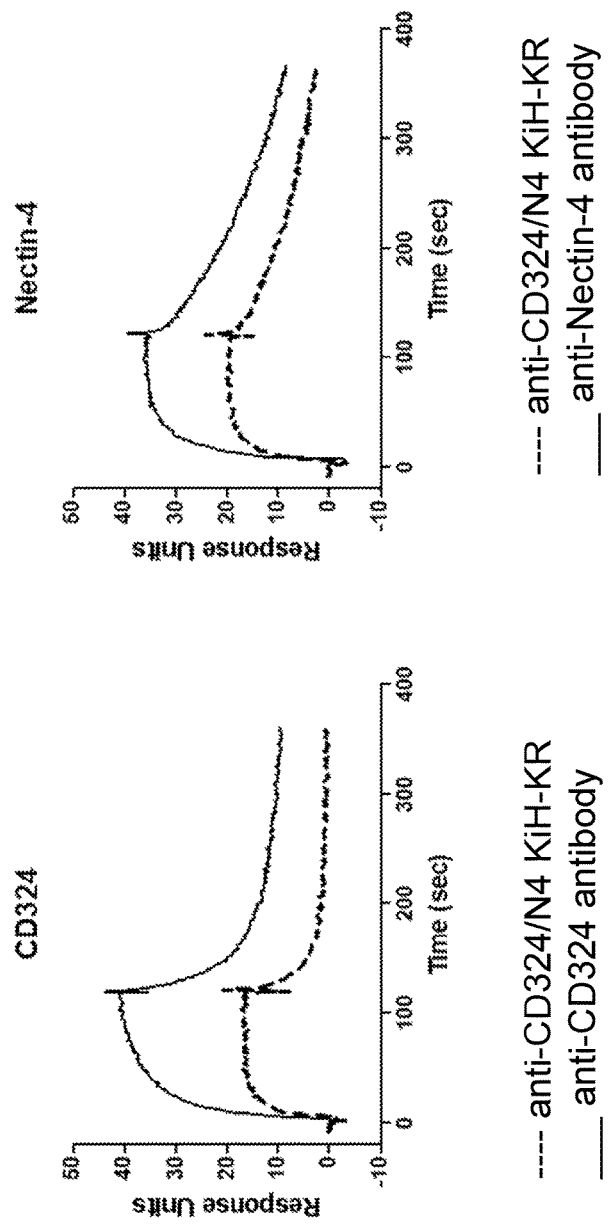

The data was processed by subtracting a control Human IgG1 surface response from the specific antibody surface response and data was truncated to the association and dissociation phase in BiaEvaluation Software 3.1 (GE Healthcare) then visualized in Prism. The equilibrium binding response (Req) was determined by averaging the response units at the end of the association phase from 115-120 sec after the beginning of antigen injection and used to calculate the percent binding of CD324 or Nectin-4 by the bispecific antibodies compared to the anti-CD324 or anti-Nectin-4 monospecific antibody control. Percent binding was determined by dividing the Req of the bispecific from the Req from the monospecific parent antibody and multiplying by a ratio of the loading RU to account for differences in loading (FIG. 4). FIGS. 4A and 4B show that the anti-CD324/N4 KiH-KR construct (see Table 3) and anti-CD324/N4 KiH-KK construct (see Table 3) retain the binding kinetics of the parent monospecific bivalent antibodies while only binding approximately half of the antigen. The anti-CD324/N4 KiH-KK exhibited 38% binding to CD324 compared to the control anti-CD324 monospecific IgG; and 56% binding to Nectin-4 protein compared to the control anti-Nectin-4 antibody (FIG. 4A). The anti-CD324/N4 KiH-KR exhibited 40% binding to CD324 compared to the control anti-CD324 monospecific IgG; and 54% binding to Nectin-4 protein compared to the control anti-Nectin-4 antibody (FIG. 4B). These data indicate that operable multispecific antibodies were assembled and retain the immunospecific binding properties of their component source antibodies.

Example 6

Mass Spectrometry Characterization of Bispecific Antibodies

The purity of bispecific anti-CD324/N4 KiH-KR and anti-CD324/N4 KiH-KK constructs (Table 3) was determined from its intact mass. The intact mass verifies that the intended bispecific antibody has been assembled correctly from four different polypeptide chains ($LC_1HC_1HC_2LC_2$). The intact mass was measured by reverse phase liquid chromatography mass spectrometry (RP-LC/MS).

The bispecific antibody samples were diluted to 2 mg/mL with 25 mM Tris, pH7.5 and then deglycosylated with 2 µL PNGaseF overnight at 37° C. RP-LC/MS analysis was performed on a Waters Acquity UPLC fitted with an Acquity UPLC BEH300 C4 (2.1×50, 1.7 um) column that was coupled to an AB Sciex 5600+. Mobile Phase A was 0.1% formic acid in water and Mobile Phase B was 0.1% formic acid in acetonitrile. A protein load of 20 μg was injected on the column and eluted with a gradient that went from 30% to 80% Phase B in 9 minutes. The column temperature was maintained at 80° C. and the flow rate was 0.2 mL/min. The mass spectrometer was operated in the positive mode and data was collected across the m/z range of 800-4000. The mass spectra from 2.8-5.3 minutes were averaged and then reconstruction was performed using Analyst software from AB Sciex.

Figures 5A, 5B:
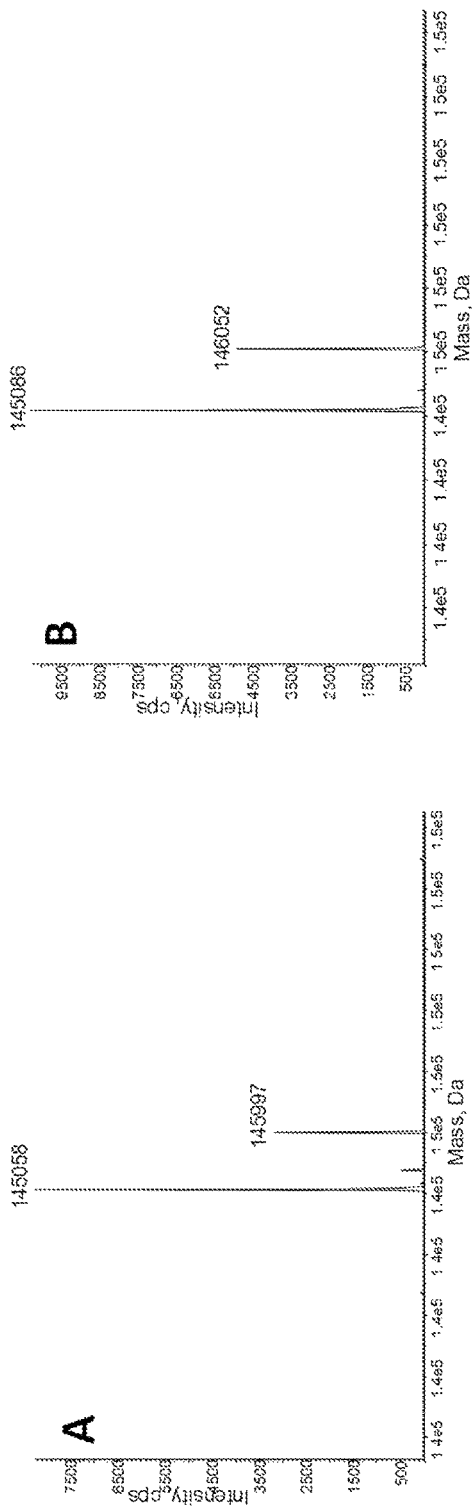
FIGS. 5A and 5B show the reconstructed, intact mass spectrums of bispecific antibodies KiH-KK (FIG. 5A) and KiH-KR (FIG. 5B) obtained by RP-LC/MS.

The deconvoluted mass spectra shown in FIGS. 5A and 5B demonstrate that the correct bispecific anti-CD324/N4 KiH-KR and anti-CD324/N4 KiH-KK constructs were produced with 69%-72% purity. A single impurity was present in both constructs at 26%-31%. The observed mass difference for the anti-CD324/N4 KiH-KK construct impurity was 940 Da which matches the expected mass difference for the incorrect light chain pairing $LC_1HC_1HC_2LC_1$ (FIG. 5A). The mass difference for the anti-CD324/N4 KiH-KR construct impurity was 966 Da which is expected for the incorrect pairing $LC_1HC_1HC_2LC_1$ (FIG. 5B).

Example 7

IgG-Fab Fusion Bispecific Antibodies

Many multispecific antibody formats have been developed for a variety of different strategies (Kontermann (2012) Mabs, 1; 4(2):182-197). In general the bispecific formats tend to fall under one of two broad categories: asymmetric IgGs, which have similar structure to standard monospecific IgGs but with binding regions that react with more than one determinant; and fusion proteins, including IgG fusion proteins which may comprise a variety of specificity/valency configurations.

Fusion protein generally employ antibody fragments for the fusion partners, such as the single chain Fv (scFv) or Fab fragment. scFv fragments are commonly used due to the simplicity of working with a single chain, as opposed to Fab fragments, where correct pairing of multiple chains can be problematic. However, when converting a parent IgG clone to an antibody fragment, reformatting to an scFv format is not always straightforward, and may require extensive engineering efforts to optimize. Fab fragments, on the other hand, are more amenable to reformatting from a parent IgG clone.

Correct pairing of heavy and light chains using residue substitutions at the CL/CH1 interface can also enable the correct pairing of different chains in a Fab format. This allows novel bispecific formats to be developed without using a common light chain, or scFv fragments. For example, FIG. 6 shows a putative IgG-Fab fusion format that employs the use of residue substitutions described in Table 2 and Table 3. A review of FIG. 6 shows two multispecific constructs (A and B) comprising tetravalent bispecific antibodies that bind discrete determinants X and Z. As with the other constructs discussed herein the selective imposition of electrostatic charges provides for the preferential assembly of the engineered multispecific antibody. Additional topologies of this IgG-Fab fusion exhibiting different imposed charge distributions are also possible, such as Fab fusion to the N or C terminus of either the heavy or light chain. Such constructs are well within the purview of the skilled artisan in light of the instant disclosure and may be fabricated without undue experimentation. Constructs such as the exemplified novel IgG-Fab fusions can be useful for other formats that currently employ scFvs but would be more effective as a Fab fragment. Instead of using scFVs, it is now possible to employ Fab fragments in their place, and CL/CH1 interface modifications to ensure correct chain pairing in the Fab.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PBD, and translations from annotated coding regions in GenBank and RefSeq cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. A bispecific bivalent antibody comprising a first binding region having a first CL domain comprising a S176K and N137K or N137R mutation, and a first CH1 domain comprising a S188D and T192D mutation; and a second binding region having a second CL domain comprising a S176D and N137D mutation and a second CH1 domain comprising a S188K and T192K mutation wherein the residues are numbered according to Kabat.

2. The bispecific bivalent antibody of claim 1 wherein said antibody further comprises a cytotoxic agent.

3. The bispecific bivalent antibody of claim 1 comprising a first binding region and a second binding region wherein said first and second binding region each comprise a light chain variable region and a heavy chain variable region from an antibody selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, and CC49, wherein the first and second binding regions are from different antibodies.

* * * * *